(12) United States Patent
Anderson et al.

(10) Patent No.: US 7,270,947 B2
(45) Date of Patent: Sep. 18, 2007

(54) METHOD FOR CONTROLLING BIOOXIDATION REACTIONS

(75) Inventors: Kevin W. Anderson, Indian Springs, OH (US); J. Douglas Wenzel, Cincinnati, OH (US)

(73) Assignee: Cognis Corporation, Ambler, PA (US)

( * ) Notice: Subject to any disclaimer, the term of this patent is extended or adjusted under 35 U.S.C. 154(b) by 385 days.

(21) Appl. No.: 10/756,240

(22) Filed: Jan. 13, 2004

(65) Prior Publication Data

US 2005/0084940 A1    Apr. 21, 2005

Related U.S. Application Data

(60) Provisional application No. 60/439,991, filed on Jan. 14, 2003.

(51) Int. Cl.
*C12Q 3/00*     (2006.01)
*C12P 7/64*     (2006.01)
*C12P 7/40*     (2006.01)
*C12P 7/44*     (2006.01)

(52) U.S. Cl. .................. 435/3; 435/134; 435/136; 435/142

(58) Field of Classification Search ............ 435/3, 435/134, 142, 924, 136
See application file for complete search history.

(56) References Cited

U.S. PATENT DOCUMENTS

| | | | |
|---|---|---|---|
| 5,254,466 | A | 10/1993 | Picataggio et al. |
| 5,962,285 | A | 10/1999 | Anderson et al. |
| 6,569,670 | B2 | 5/2003 | Anderson et al. |

OTHER PUBLICATIONS

U.S. Appl. No. 09/663,963, filed Sep. 19, 2000, Anderson et al.
Dixon, "Viable but Nonculturable", ASM NEWS, vol. 64, No. 7, (1998), pp. 372-373.
Rehm, et al., "Mechanisms and Occurrence of Microbial Oxidation of Long-Chain Alkanes", Adv. Biochem Eng., vol. 9, (1981), pp. 175-215.
Picataggio, et al., "Metabolic Engineering of *Candida tropicalis* For The Production Of Long-Chain Dicarboxylic Acids", BIO/TECHNOLOGY, vol. 10, (Aug. 1992), pp. 894-898.
Gallo, et al., "Alkane Oxidation In *Candida tropicalis*", Biochimica et Biophys. Acta., vol. 296, (1973), pp. 624-638.
Kemp, et al., "Inducible long chain alcohol oxidase from alkane-grown *Candida tropicalis*", Applied Microbiology and Biotechnology, vol. 29, Springer-Verlag, (1988), pp. 370-374.
Scheller, et al., "Oxygenation Cascade in Conversion of n-Alkanes to $\alpha,\omega$-Dioic Acids Catalyzed by Cytochrome P450 52A3", The Journal of Biological Chemistry, vol. 273, No. 49, (1998), pp. 32528-32534.
Eschenfeldt, et al., "Transformation of Fatty Acids Catalyzed by Cytochrome P450 Monooxygenase Enzymes of *Candida tropicalis*", Applied and Environmental Microbiology, vol. 69, No. 10, (Oct. 2003), pp. 5992-5999.
Wackett, et al., Biocatalysis and Biodegradation, Chapter 2, ASM Press, (2001), pp. 15-18.
Stryer, Biochemistry—Danger lurks in the reduction of oxygen, 4th Edition, W. H. Freemen and Co., (1999), p. 540.
Hosobuchi, et al., "Application of Computer to Monitoring and Control of Fermentation Process: Microbial Conversion of ML-236B Na to Pravastatin", Biotechnology and Bioengineering, vol. 42, No. 7, John Wiley & Sons, Inc., (Sep. 20, 1993), pp. 815-820.
Lee, et al., "Control of fed-batch fermentations", Biotechnology Advances, vol. 17, Elsevier Science Inc., (1999), pp. 29-48.
Coppella, et al., "Low-Cost Computer-Coupled Fermentor Off-Gas Analysis via Quadrupole Mass Spectrometer", Biotechnology and Bioengineering, vol. 29, John Wiley & Sons, Inc., (Apr. 1987), pp. 679-689.

*Primary Examiner*—Herbert J. Lilling
(74) *Attorney, Agent, or Firm*—John F. Daniels; Daniel S. Ortiz

(57) ABSTRACT

Biooxidation reactions can be controlled by a method which comprises the steps of: (1) independently adding a substrate and a co-substrate at predetermined rates to a bioxidation reaction mixture comprised of a biocatalyst; (2) measuring the oxygen consumption rate and carbon dioxide evolution rate from the reaction mixture; (3) determining the instantaneous rates of substrate and cosubstrate consumption by solving simultaneous equations relating carbon dioxide evolution rate and oxygen consumption rate to the substrate oxidation stoichiometry, the cosubstrate combustion stoichiometry, and optionally the biomass formation stoichiometry; (4) simultaneously adjusting the substrate and cosubstrate addition rates to the rates of substrate oxidation and cosubstrate consumption in order to maximize the rate of product formation while simultaneously minimizing the rate of cosubstrate usage. The method provides a rapid means of controlling fed-batch biooxidation reactions which can employ in-line techniques and is broadly applicable for diverse oxidation reactions.

14 Claims, 10 Drawing Sheets

R = any constituent having and oxidizable -CH3 group
= the terminal end of an alkane or alkene with a total of 9-20 carbons
= the carboxylic acid end of saturated or unsaturated fatty acid with a total of 9-20 carbons

FIGURE 3

*Cytochrome P450 /*
*Cytochrome P450 Reductase*
$$R\text{-}CH_3 + O_2 + NADPH + H^+ \longrightarrow R\text{-}CH_2OH + H_2O + NADP^+$$

*Fatty Alcohol Oxidase*
$$R\text{-}CH_2OH + O_2 \longrightarrow R\text{-}CHO + H_2O_2$$

*Catalase*
$$H_2O_2 \longrightarrow H_2O + \tfrac{1}{2} O_2$$

*Aldehyde Dehydrogenase*
$$R\text{-}CHO + NAD^+ + H_2O \longleftrightarrow R\text{-}COOH + NADH + H^+$$

---

*Net ω-oxidation reaction*
$$R\text{-}CH_3 + 1\tfrac{1}{2} O_2 + NADPH + NAD^+ \longrightarrow R\text{-}COOH + NADP^+ + NADH + H_2O$$

METHOD FOR CONTROLLING BIOOXIDATION REACTIONS

CROSS-REFERENCE TO RELATED APPLICATIONS

This application claims the benefit of copending provisional application Ser. No. 60/439,991, filed on Jan. 14, 2003, the entire contents of which is incorporated herein by reference.

STATEMENT REGARDING FEDERALLY SPONSORED RESEARCH OR DEVELOPMENT

This invention was funded, at least in part, under a grant from the Department of Commerce, NIST-ATP Cooperative Agreement Number 70NANB8H4033. The Government may therefore have certain rights in the invention.

BACKGROUND OF THE INVENTION

Enzymes and microorganisms, through the direct reduction of molecular oxygen, naturally catalyze wide ranges of oxidation reactions. These highly irreversible reactions can be regarded as quite violent from a biochemical perspective liberating much free energy of reaction as heat. The fundamental mechanism by which the many diverse biooxidations of organic substrates occur can generally be regarded as, first, the activation of molecular oxygen to form a highly reactive oxygen species. This is followed by a shift of electrons from the substrate to the activated oxygen species resulting in the net oxidation of the substrate. The original oxygen atoms from molecular oxygen may or may not be incorporated into the organic substrate to make the desired oxidation product. The reaction may be catalyzed by a single enzyme or through the coordinated action of multiple enzymes. Many enzyme and enzyme systems comprising, cytochromes, monooxygenases, dioxygenases, desaturases, and oxidases are capable of harnessing the reactive power of molecular oxygen for the oxidation of organic substrates with a selectivity and specificity unparalleled by classical chemical synthesis.

There is much incentive to exploit these reactions by applying them to ordinary chemical substrates by adding one or more chemical functionalities at particularly desirable positions in the substrate molecule. Owing to the selectivity and specificity of certain biocatalysts, many chemical reactions and purification steps with their concomitant product and substrate losses can be eliminated. Alternatively, these reactions can aid the degradation of unwanted chemical products, again by adding functionality to the molecule making it easier to sequester for disposal or degrade further in subsequent transformation steps.

There are many barriers to overcome in successfully operating these reactions for commercial purposes. The generation of highly reactive oxygen species is, in metabolic terms, a violent reaction. These reactive intermediates can damage or degrade the biocatalyst, destroy the enzymatic activity sought for making the desired transformation, or react non-selectively with the substrate. As pointed out by Stryer in his text "Biochemistry"—*Danger lurks in the reduction of oxygen*. Organisms utilizing molecular oxygen possesses enzymes and enzyme systems for scavenging renegade oxygen radicals in nature. In the rapid biooxidation reactions occurring in industrial fermentations, such radicals may overwhelm the naturally occurring levels of these scavenging systems. As a result, in biooxidation reactions involving viable cells, it is common to observe a rapid decay in cell viability and the recovery of viable cells (Dixon, B., "Viable but Nonculturable", ASM News, 64, pgs. 372-373, 1998).

Wide ranges of organic molecules are potential substrates for bio-oxidation, without limitation to the natural substrate preference of the oxidation pathway, to make many oxidation products. Certain characteristics of the substrate may dictate how it will be combined with the oxidation catalyst to effect the oxidation. The substrate may 1) be toxic, deactivating the catalyst,
2) be volatile and susceptible to losses in the fermentor off-gases,
3) repress its own oxidation,
4) induce or cause unwanted side reactions,
5) be expensive; committing large quantities of substrate to the vessel adds risk should the batch fail through equipment failure or contamination,
6) generate non-selective oxidation reactions or other reactions,
7) cause problems in recovering or purifying the product,
8) may form flammable mixtures with air.

For these reasons, it is often desirable to add the substrate continuously or in discretely metered increments during the fermentation in a fed-batch-operating mode to minimize substrate accumulation.

Despite the large amount of free energy thermodynamically available from many biooxidation reactions, these reactions tend to be highly irreversible liberating much of the free energy of reaction as heat rather than as forms useful for metabolic work. This is due to the initial metabolic energy input required to create the reduced oxygen species from molecular oxygen. To generate this needed metabolic energy driving the desired biooxidation reaction and maintaining the biocatalyst, a second substrate is supplied to the reaction system. This second substrate is frequently called the co-substrate and may be selected from any of a number of fermentable compounds in common use for fermentation, for example, sacharrides, organic acids, alcohols, or hydrocarbons. As for similar reasons with the bio-oxidation substrate, it may be desirable to add the co-substrate continuously or in discretely metered increments to minimize accumulation of the co-substrate.

Some control of substrate concentration is known in the art. For example, the concentration of the substrate ML236B Na was controlled in a cytochrome P450 mediated hydroxylation reaction to make pravastatin. A crossflow filtration module and peristaltic pump generated a filtrate. This filtrate was periodically analyzed by automatic HPLC to give near real time measurement of ML236B Na concentration in the aqueous reaction mixture.

The crossflow system worked well with the soluble substrate apparently because the strain did not form large pellets and no oily substances were present in the reaction mixture. No control however was applied to the cosubstrate 50% glucose feed which was maintained constant over the course of the reaction.

Thus there is a need for methods for simultaneously controlling the addition of multiple feed streams in the field of biooxidations. Biooxidation substrates, cosubstrates, and products are frequently complex molecules that may be sparingly soluble in aqueous systems that, together with the biocatalyst, constitute a complex reaction matrix. While a variety of analytical techniques may be applied offline for the analysis of products, substrates, and co-substrates, such methods tend to be laborious and of little value for real-time control of nutrient feed in these fed-batch reactions. One is therefor motivated to seek rapid computerized methods for simultaneously controlling the substrate and cosubstrate feeds to biooxidation reactions.

In contrast, the gas phase is a relatively simple matrix for which a variety of instruments are available to give gas phase composition measurements. When coupled with a measurement of gas flow to and from the biooxidation reaction, the overall and component gas phase balances provide real time measurement of carbon dioxide evolution rate (CER) and oxygen uptake rate (OUR).

The concept of controlling nutrient feeds in fed batch fermentations using component gas balances is known in the art. In particular, gas component balance measurements have been used to calculate and control substrate concentration or to control specific growth rate.

BRIEF DESCRIPTION OF THE SEVERAL VIEWS OF THE DRAWINGS

FIG. 3 shows a stoichiometric model based on literature data of steps in the ω-oxidation pathway leading to the, net reaction used to determine biooxidation stoichiometric parameters. Three of the steps involve molecular oxygen.

SUMMARY OF THE INVENTION

Figure 1:
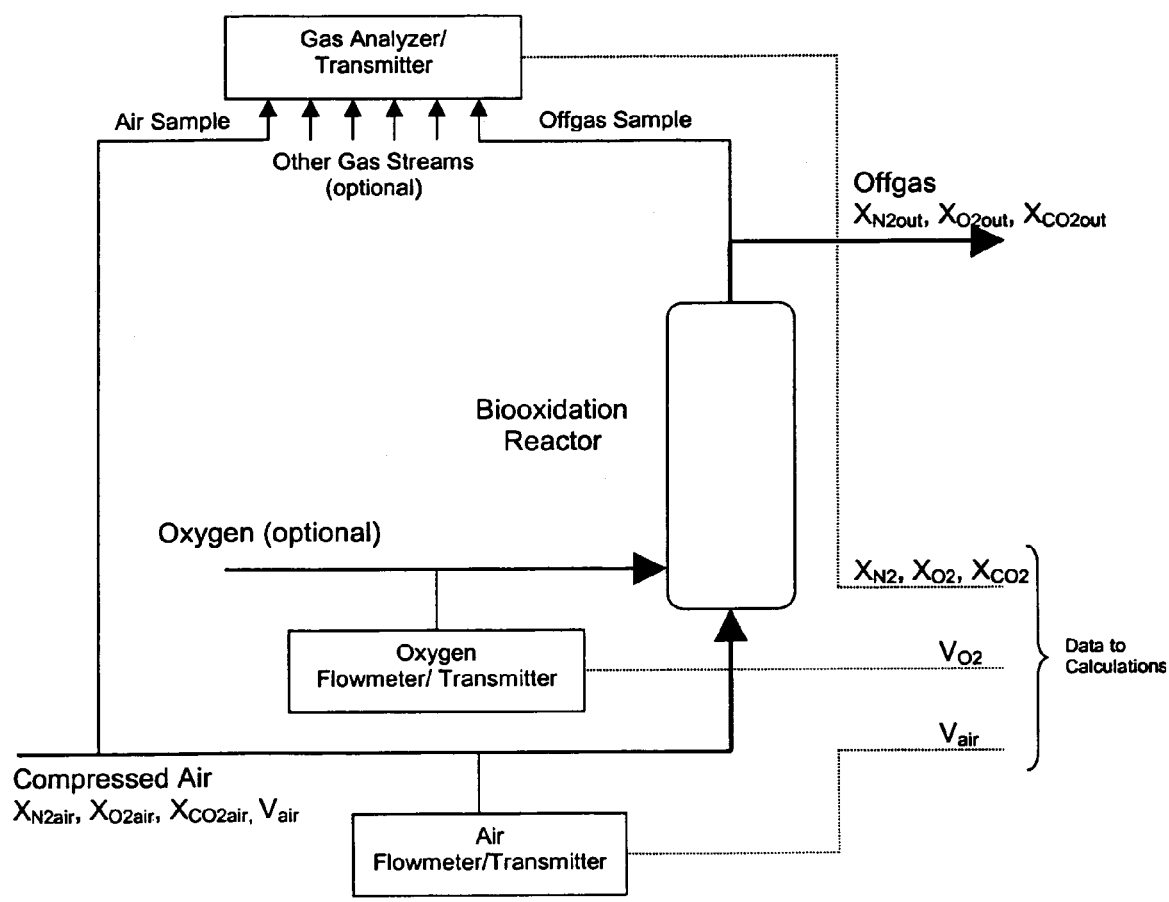
FIG. 1 shows a flow diagram of gases entering and leaving a biooxidation reactor with typical location of instruments used in measurements for in-line component gas balance calculations. Also shown is alternative locations for the use of optional pure oxygen supplementation.

The present invention relates to a method for controlling a biooxidation reaction comprising the steps of: (1) independently adding a substrate and a co-substrate at predetermined rates to a biooxidation reaction mixture comprised of a biocatalyst; (2) measuring the oxygen consumption rate and carbon dioxide evolution rate from the reaction mixture; (3) determining the instantaneous rates of substrate and cosubstrate consumption by solving simultaneous equations relating carbon dioxide evolution rate and oxygen consumption rate to the substrate oxidation stoichiometry, the cosubstrate combustion stoichiometry, and optionally the biomass formation stoichiometry; (4) simultaneously adjusting the substrate and cosubstrate addition rates to the rates of substrate oxidation and cosubstrate consumption in order to maximize the rate of product formation while simultaneously minimizing the rate of cosubstrate usage.

The method according to the invention provides a rapid means of controlling fed-batch biooxidation reactions which can employ computerized techniques and is broadly applicable for diverse reactions. There is no need to utilize highly accurate kinetic models as has been the case with known methods. Neither do the stoichiometric models used to define the equilibrium state according to the present invention have to be highly accurate. The stoichiometric models only need to be reflective of the biooxidation reaction for defining the prevailing equilibrium state, since the substrate and cosubstrate feed rates follow an operating line relative to the stoichiometric line. In contrast to some prior art methods developed for manipulating a limiting nutrient for controlling growth of microorganisms, the method according to the invention does not attempt to control substrate or cosubstrate concentration in the biooxidation reaction, which may be immeasurable by methods suited for routine process control purposes.

The present invention further provides methods and examples for determining the needed reaction stoichiometry from literature or biochemical pathway information when available. In the absence of such data or where conflicting data exists, then methods and examples are further provided for determining reaction stoichiometry using independent experiments.

The present invention also provides for a method for determining product accumulation in the biooxidation reaction. It has been found that the methods according to the invention are easy to implement and are sufficiently accurate to eliminate the need for offline sample analysis during the biooxidation. It has also been found that the methods of this invention to be indispensable in monitoring and maintaining biooxidation activity and reviving or returning to control a biooxidation reaction following a process upset.

DETAILED DESCRIPTION OF THE INVENTION

The term biocatalyst as used herein, means a microorganism, or an enzyme, an enzyme system, or an enzyme pathway for an in vivo biooxidation supplied with any applicable cofactors for in vitro biooxidations or biooxidations in whole organisms not recoverable as viable by traditional means known in the art for assessing viability.

While the method according to the invention can be used preferably for controlling the biooxidation of organic substrates to carboxylic acids, it can be used for the biooxidation of any type of substrate. Such substrates include, but are not limited to, alkanes, alkenes, alcohols, aldehydes, carboxylic acids and carboxylic acid derivatives such as esters, amides, anhydrides and acyl halides.

A biooxidation reaction can be considered to be composed of three simultaneous reactions: (1) the oxidation of substrate to desired product; (2) the combustion of cosubstrate to provide energy; (3) the anabolic processes of growth to make biomass from co-substrate. It has been found that while the process of Reaction 1 is clearly the desirable product forming reaction, it is the energy generating Reaction 2 that is of paramount importance in biooxidation reactions.

Many biooxidation reactions are indeed conducted using "stationary phase" or "resting" cells for which the rate of reaction 3 is zero. Yet there are many important examples of biooxidation reactions where the product accumulates intracellularly or is otherwise growth associated. In these cases, sufficient additional co-substrate is provided to generate the necessary biomass.

Reaction stoichiometry establishes a system of related rates from which the relative velocities of reactions 1-3 can be instantaneously determined from measurements of the oxygen uptake rates and carbon dioxide evolution rates. The reaction velocities are instantly useful in monitoring the progress of the biooxidation. The individual reaction rates are then used to determine the instantaneous consumption rates of substrate and cosubstrate. The resulting substrate and cosubstrate consumption rates are then viewed as defining an equilibrium or stoichiometric state. Substrate and cosubstrate feed rates then follow an operating line relative to this stoichiometric state. Separate operating and equilibrium lines are constructed for the substrate and cosubstrate feed in the biooxidation reaction.

In this respect, the methods of this invention are somewhat analogous to those commonly used to describe, for example, distillation, solvent extraction, and humidification operations where the progress of those operations follow an operating line relative to an equilibrium state. Indeed, many of the principles and terminology associated with those unit operations can be applied here. Like in those examples, the equilibrium line is only rarely a straight line and it has been found the so-defined equilibrium state of biooxidation reactions to have substantial curvature, particularly where the biooxidation activity is part of an inducible pathway. Other effects causing curvature in the equilibrium line include decay in oxidation activity, dissolved oxygen and other nutrient-limitation effects, and changes in the rheological properties of the reaction system. These effects can all be observed and compensated for using the methods of this invention to maintain the biooxidation reaction at maximum performance.

In monitoring the biooxidation reaction, a graphical construction is conveniently used to describe key elements of this invention. There are many alternative ways to implement and define the stoichiometric formulas that comprise the biooxidation reaction. The strategy is similar in all cases where the biooxidation stoichiometry is represented as the superposition of the biooxidation reaction, the energy-producing combustion of cosubstrate, and optionally the formation of biomass. The rates of oxygen consumption and carbon dioxide evolution are represented as the sum of their sources from each reaction based on reaction stoichiometry. The resulting simultaneous equations are solved to give the rates of the individual reactions in terms of the product or substrate selected to define the reaction rate.

Having determined the individual rates of reaction, then the rates of substrate and cosubstrate consumption are determined as the sum of their consumption rates for each reaction. These reaction rates define the equilibrium state and for a given biooxidation reaction will follow some curve, or equilibrium line, over the duration of the reaction. If the substrate and cosubstrate feed rates are expressed in the same terms as the equilibrium state then it too will follow a path relative to the equilibrium line, usually some multiple of the equilibrium line. This multiple is called the slope of the operating line, which may be changed during the biooxidation reaction as needed to maintain the reaction rate and generate the desired final broth composition.

As a convention in describing this invention, rates of formation are taken as positive. Then the term for carbon dioxide evolution rate, or CER is $r_{CO_2}$ and the term for oxygen uptake rate, or OUR, is $-r_{O_2}$. The definition of symbols and exemplary units used in this invention is given in Table 1. Any consistent units of measure may be used with this invention.

There are many ways to approach setting up the system of biooxidation related rates. According to the general view described above, the bioxidation reaction is the sum of the three reactions having a biooxidation component, an energy generation component, and a biomass formation component. It has been found it advantageous to break the overall reaction down in this way because it makes the computerized data generated by using the methods of this invention physically and physiologically relevant. This is advantageous when dealing with process upsets.

The general stoichiometry of the biooxidation component may be represented according to Reaction 1 where a substrate or mixture of substrates is oxidized to products. A portion of the cosubstrate may also be consumed in modifying the substrate into its final product form. Reaction 1 is therefore the net of multiple reactions associated with synthesis of the products having a rate $r_{1a}$.

Reaction 1

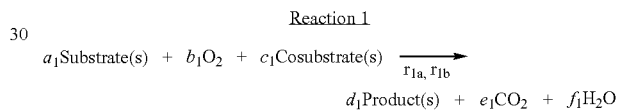

$$a_1 \text{Substrate(s)} + b_1 O_2 + c_1 \text{Cosubstrate(s)} \xrightarrow{r_{1a}, r_{1b}} d_1 \text{Product(s)} + e_1 CO_2 + f_1 H_2O$$

TABLE 1

Definition of Mathematical Variables and Symbols

| Symbol | Exemplary units | Definition |
|---|---|---|
| $A_1$ | dimensionless | Ratio substrate feed to substrate demand, slope of substrate operating line |
| $A_2$ | dimensionless | Ratio substrate feed to substrate demand, slope of substrate operating line |
| $A_3$ | dimensionless | Ratio substrate feed to substrate demand, slope of substrate operating line |
| $A_4$ | dimensionless | Ratio substrate feed to substrate demand, slope of substrate operating line |
| $F_s$ | | Actual substrate feed rate |
| $F_s$(setpoint) | g/hr | Substrate feed rate setpoint |
| $F_C$(setpoint) | g/hr | Co-substrate feed rate setpoint |
| $-r_1$ | mgmole substrate/kg/hr | Rate of substrate consumption by Reaction 1 |
| $-r_{1a}$ | mgmole $O_2$/kg/hour | Rate of oxygen consumption by Reaction 1 (Example 11) |
| $-r_{1a}$ (theoretical) | mgmole $O_2$/kg/hour | Substrate feed rate $F_s$ expressed as an oxygen consumption rate (Example 11) |
| $-r_2$ | mgmole co-substrate/kg/hr | Rate of co-substrate consumption by Reaction 2 |
| $r_{2a}$ | mgmole $CO_2$/kg/hour | Rate of carbon dioxide production by Reaction 2 (Example 11) |
| $r_{2a}$ (theoretical) | mgmole $CO_2$/kg/hour | Co-substrate feed rate $F_C$ expressed as a carbon dioxide evolution rate |
| $r_3$ | mgmole biomass/kg/hr | Rate of biomass formation |
| $r_4$ | mgmole biomass/kg/hr | Rate of biomass formation |
| $-r_5$ | mgmole co-substrate/kg/hr | Rate of co-substrate consumption by reaction 5 |

TABLE 1-continued

Definition of Mathematical Variables and Symbols

| Symbol | Exemplary units | Definition |
|---|---|---|
| $r_{CO2}$ | mgmole $CO_2$/kg/hour | Rate of carbon dioxide production; CER |
| $-r_{O2}$ | mgmole $O_2$/kg/hour | Rate of oxygen consumption; OUR |
| $-r_C$ | mgmole cosubstrate/kg/hr | rate of cosubstrate consumption |
| $-r_S$ | mgmole substrate/kg/hr | rate of substrate consumption |
| $r_{H2O}$ | mgmole water/kg/hr | rate of water formation |
| $M(t)$ | kg | Actual mass of reaction mixture as a function of time (Example 15) |
| $Y_{P/X}$ | g Product/g Biomass | mass of product in a unit mass of dry biomass |
| $Mw_c$ | g/gmole | formula weight of the cosubstrate |
| $Mw_P$ | g/gmole | formula weight of product |
| $Mw_X$ | g/gmole | formula weight of biomass |
| $Mw_S$ | g/gmole | formula weight of substrate |
| $MW_{diacids}$ | g/gmole | formula weight of diacids (Example 15) |
| $X_c$ | g/g | Mass fraction metabolizable substances in the co-substrate feed |
| $X_s$ | g/g | Mass fraction metabolizable substances in the co-substrate feed |
| $X_{diacids}$ | g/kg | Diacid concentration in fermentation broth (Example 15) |
| $V_f$ | kg | biooxidation reaction mass |
| $a_i$ | dimensionless | Stoichiometric coefficient of substrate in reaction i |
| $b_i$ | dimensionless | Stoichiometric coefficient of oxygen in reaction i |
| $c_i$ | dimensionless | Stoichiometric coefficient of cosubstrate in reaction i |
| $d_i$ | dimensionless | Stoichiometric coefficient of products in reaction i |
| $e_i$ | dimensionless | Stoichiometric coefficient of carbon dioxide in reaction i |
| $f_i$ | dimensionless | Stoichiometric coefficient of water in reaction i |
| $g_i$ | dimensionless | Stoichiometric coefficient of biomass in reaction i |
| $\Psi$ | | Terms collected in equation 5 defined by equation 6 |
| $t$ | hours | time |

A second simultaneous reaction is concerned with the generation of energy to maintain the cells and drive the biooxidation reaction. This is the cosubstrate combustion stoichiometry having a rate $r_{2a}$.

Reaction 2

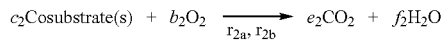

$$c_2 \text{Cosubstrate(s)} + b_2 O_2 \xrightarrow{r_{2a}, r_{2b}} e_2 CO_2 + f_2 H_2O$$

Reaction 3 is associated with the formation of biomass important in the preparation of growth associated biooxidation products.

Reaction 3

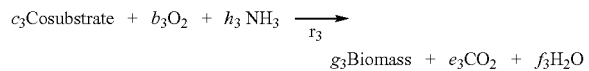

$$c_3 \text{Cosubstrate} + b_3 O_2 + h_3 NH_3 \xrightarrow{r_3} g_3 \text{Biomass} + e_3 CO_2 + f_3 H_2O$$

With respect to biomass formation Reaction 3, it has been found to be useful to further subdivide this reaction into component parts, in a sense into its net catabolic reactions and net anabolic reactions. Subtracting a stoichiometric reaction based on either oxygen or carbon dioxide that represents combustion of the cosubstrate eliminates either the oxygen or the carbon dioxide from the biomass formation reaction. Here, subtracting the stoichiometric carbon dioxide, the amount of cosubstrate devoted to biomass formation is given by Reaction 4, and the energy component of growth is given by Reaction 5.

Reaction 4

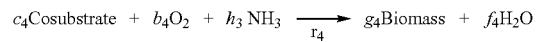

$$c_4 \text{Cosubstrate} + b_4 O_2 + h_3 NH_3 \xrightarrow{r_4} g_4 \text{Biomass} + f_4 H_2O$$

Reaction 5

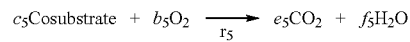

$$c_5 \text{Cosubstrate} + b_5 O_2 \xrightarrow{r_5} e_5 CO_2 + f_5 H_2O$$

Reaction 5 and Reaction 2 are the same energy generating reactions. It is not necessary in utilizing this invention to distinguish how the cell is utilizing the energy. It is only important to provide sufficient cosubstrate for biomass formation, if needed, and to account for the net evolution or consumption of oxygen or carbon dioxide. It is also important to note with respect to Reaction 4 that the stoichiometric coefficient on oxygen may have a positive or negative value depending on the nature of the cosubstrate. The stoichiometric coefficients are determined using information from the literature, knowledge of the physiological pathway, or determined by independent experiments.

Having defined the biooxidation reaction according to its principal simultaneous Reactions 1, 2 and 4, it is now possible to derive the reaction rate formulas in terms of gas component balances. The oxygen balance is then given by Equation 1.

$$-r_{O2} = OUR = (b_4/g_4)r_{4a} - (b_1/a_1)r_{1a} - (b_2/c_2)r_{2a} \qquad \text{Equation 1}$$

Similarly, the carbon dioxide balance is given by Equation 2.

$$r_{CO2} = CER = (e_1/a_1)(-r_{1a}) - (e_2/c_2)r_{2a} \qquad \text{Equation 2}$$

For the growth-associated products, then a certain biomass generation rate is sought relative to product. Especially for intracellular products, the biomass is said to contain a certain mass fraction of product as a part of the total. For that fraction of biomass that needs to be generated during the biooxidation reaction, then $$Y_{P/X}(Mw_X/Mw_P) = \frac{(d_1/a_1)Mw_P(-r_{1a})}{r_{4a}Mw_X + (d_1/a_1)Mw_P(-r_{1a})} \qquad \text{Equation 3}$$

Equations 1-2 constitute a system of equations with 2 unknowns to be solved simultaneously, using the constitutive equation 3, for the rates of each component reaction comprising the biooxidation. Then first solving for the rate of reaction 2 using equation 2 gives Equation 4

$$-r_{2a} = (c_2/e_2)[r_{CO2} - (e_1/a_1)(-r_{1a})]. \qquad \text{Equation 4}$$

Solving for the rate of Reaction 4 using equation 3 then gives $$r_{4a} = (d_1/a_1)\Psi(-r_{1a}) \qquad \text{Equation 5}$$

where, $$\Psi = (Mw_P/Mw_X)(1/Y_{P/X})[1 - Y_{P/X}] \qquad \text{Equation 6}$$

Finally solving Equation 1 for the rate of Reaction 1 using equations 4-6 gives $$-r_{1a} = \frac{-r_{O2} - (b_2/e_2)r_{CO2}}{(b_1/a_1) - (b_2/e_2)(e_1/a_1) + (b_4/g_4)(d_1/a_1)\Psi} \quad \text{Equation 7}$$

Having the in-line component gas balance values of CER and OUR, then the rates of the individual reactions can be explicitly determined first using equation 7, then equations 4 and 5. Then the rate of substrate and cosubstrate utilization can be determined, which defines an equilibrium reaction state as given by Equations 8 and 9 respectively.

$$-r_s = -r_{1a} \quad \text{Equation 8}$$

$$-r_c = (c_4/g_4)r_{4a} - (c_1/a_1)r_{1a} - r_{2a} \quad \text{Equation 9}$$

Plots of $-r_s$ and $-r_c$ versus time during the course of the fermentation results in the previously described equilibrium or stoichiometric lines for the substrate and cosubstrate respectively.

The substrate feed rate is then determined from the substrate operating line according to equation 10.

$$F_s = 0.001 A_1 (Mw_s/X_s)(-r_s)V_f \quad \text{Equation 10}$$

A plot of $F_s X_s Mw_s/V_f$ versus time defines the operating line for the substrate. In principle, if a value of 1.0 is selected for the slope of the operating line then the rate of substrate addition will equal the rate of substrate consumption. In practice it has been found to be beneficial to operate biooxidations either at values of the operating line slope above or below 1.0 depending on what phase the biooxidation reaction. This is particularly true when the biooxidation reaction is part of an inducible pathway and especially when the substrate is the inducer.

Equation 10 is suitable for use in defining a setpoint for controlling the substrate feed rate in an automated system. Satisfactory results have been obtained by manually making periodic substrate feed rate adjustments to maintain the desired operating line relative to the equilibrium line.

Similarly, the cosubstrate feed rate is then determined from the cosubstrate operating line according to equation 11.

$$F_c = 0.001 A_2 (Mw_c/X_c)(-r_c)V_f \quad \text{Equation 11}$$

A plot of $F_c X_c Mw_c/V_f$ versus time defines the operating line for the cosubstrate. In principle, if a value of 1.0 is selected for the slope of the operating line, then the rate of cosubstrate addition will equal the rate of substrate consumption. In practice it has been found to be beneficial to operate biooxidations either at values of the operating line slope above or below 1.0 depending on what phase the biooxidation reaction. This is particularly true when the biooxidation reaction is part of an inducible pathway and especially when the substrate is the inducer. Operating the biooxidation at values of the operating line slope less than 1.0 can increase the velocity of Reaction 1 and save cosubstrate, but usually at the cost of biocatalyst longevity.

Equation 11 is suitable for use in defining a setpoint for controlling the cosubstrate feed rate in an automated system. Satisfactory results have been obtained using manual control by making periodic substrate feed rate adjustments to maintain the desired operating line relative to the equilibrium line.

Similarly, the cosubstrate feed rate is then determined from the cosubstrate operating line according to equation 11.

This general case biooxidation reaction process control strategy has broad utility in controlling biooxidation reactions. It is well suited for implementation in computer controlled facilities with a flexible control system capable of executing the strategy. An alternative approach has been found that can be immediately executed in laboratory and multipurpose facilities having the capability to provide component gas balance data without the need for substantial reprogramming in the facility. It is clear that many alternative expressions of the operating line and equilibrium line are possible by choosing alternative definitions of the individual reaction rates and subdividing the component reactions of the biooxidation.

Method 1 has the advantage that reaction rates are expressed directly in terms of substrate and cosubstrate consumption. It is a more exact treatment and is the preferred method applicable to a broad range of biooxidations. An alternative method that gives suitable results is given as Example 11 for those who wish to immediately test this invention.

The reaction rates $r_i$ are customarily expressed on a mass or volumetric basis, for example mgmoles/kg/hr or mgmoles/liter/hr. It has been found it is somewhat unwieldy and unnecessary in practice to use these directly as expressions for the operating and equilibrium lines. Substrate and cosubstrate are fed to the whole biooxidation reaction mixture not just one kg or one liter at a time. However, since it is desirable to control the substrate and cosubstrate feed to a biooxidation reaction it is expected that the mass or volume of the reaction mixture might change appreciably during the course of the reaction. It has been therefore found to be useful to express the reaction rates in terms of the product $r_i \cdot V_f$, which then gives rates of formation in terms of mgmoles/hr for the whole biooxidation mixture. It is preferred then to modify the operating line, stoichiometric line, and feed rate formulas by multiplying both sides of the formula by $V_f$. Another advantage of this alternative expression for the reaction rates is that the biooxidation reactor need not be equipped with a measurement device providing instantaneous measurements of the reaction mass or volume in order to make use of this invention.

In facilities using the customary expressions for rates of reaction for expressing $r_{CO2}$ and $-r_{O2}$, then a value of 1 kg or 1 liter may be entered for the user-defined reaction volume to give these rates of reaction in mgmoles/hr. Alternatively, to the preference of the user, a value of 1000 may be entered to give gmoles/hr; a value of 454,000 gives lbmoles/hr; a value of 1,000,000 gives kgmoles/hr. This method makes comparison of similar biooxidation reactions done at different scales of operation difficult to compare. In this case it has been determined to be useful to further modify the rate expression by dividing by a quantity $V^o$, that is a standard mass or volume that characterizes the scale of the batch. The reaction rates are then expressed in terms of the product $r_i \cdot V_f/V^o$. This now returns the rate expression to the more customary units. In principle, a good choice for $V^o$ is the mass of biocatalyst charged to the biooxidation reaction mix. In practice, to the extent that the relative biocatalyst charge is similar from batch to batch, then a characteristic mass or volume of reaction may be chosen. Typical values may be the starting mass used to prepare the biocatalyst, the mass of the reaction mixture prior to starting the biooxidation, or the sum total of all reagents anticipated to be charged to the batch. For biooxidation reactions integrated with a growth phase that generates the biocatalyst, it has been found that choosing $V^o$ as the initial mass of production media charged to the reactor sufficient for comparing different scales of operation spanning 0.01 m3 to >100 m3. This alternative expression has the advantage that it gives comparable and immediately recognizable results when the same reaction is conducted in facilities having reactors of different sizes.

It is noteworthy that water of reaction does not enter into the stoichiometric line, operating line, or control formulas. Those formulas only depend on the stoichiometric relationships between substrate, cosubstrate, biomass, oxygen, and carbon dioxide. Indeed, this is true for example, if partial combustion products are formed from cosubstrate, or if a portion of the substrate is cleaved to release an unmetabolized coproduct. The control strategies presented here remain valid, but like water of reaction, these accumulate in the reaction mixture.

Biooxidation reactions conducted in aqueous media already have water in large excess, but water of reaction remains important in the overall material balance of the reaction. The water of reaction carries added importance, for example, for biooxidation reactions conducted in non-aqueous systems. It is then useful to monitor the rate of water formation, which may be calculated based on the reaction formulas subject to the related stoichiometric relationships.

$$r_{H2O} = (f_1/a_1)r_{1a} + (f_2/c_2)r_{2a} + (f_4/g_4)r_{4a} \quad \text{Equation 20}$$

The areas under the stoichiometric lines during an interval of time give the cumulative production of the reaction component over that interval of reaction time. Application of reaction stoichiometry then gives the cumulative production of the other reaction components and cumulative addition of feed. The discrete data are integrated numerically to solve the necessary integral. It has been found using trapezoid rule gives satisfactory results. This principle is instantly useful for determining the stoichiometry of a biooxidation reaction when the stoichiometry is not known or there is uncertainty in stoichiometric data available from the literature. It has been further found that, if a measurement of the reaction mass is available, then the concentration of product may be determined by integration from the start of the biooxidation reaction to any point during the reaction. This substantially reduces the amount of off-line sample analysis needed to monitor the biooxidation reaction.

The following examples are meant to illustrate but not to limit the invention.

EXAMPLE 1

Component Gas Balance Calculations with Optional Oxygen Supplementation

It is the objective in this example to provide the expressions for $r_{CO2} \cdot V_f$ and $-r_{O2} \cdot V_f$ in terms of readily measured fermentation parameters for use in the control strategies of this invention. The mathematical formulas executed in determining rate of carbon dioxide evolution and rate of oxygen uptake for use in the methods of this invention are presently derived from gas phase component balances. A simplified flow diagram of the biooxidation reactor gas flow system for use in defining the component gas balance calculations is shown in FIG. 1 where a gas containing oxygen, usually air, is sparged into the reaction mixture. Optionally, a supplementary supply of oxygen may be blended with the air to enrich its oxygen content or sparged directly into the biooxidation reactor. The component gas balance equations are valid and algebraically the same irrespective of the feed location chosen for either the air or the optional oxygen supplies. The combined gases contact the reaction mixture become somewhat depleted of oxygen and enriched in carbon dioxide and moisture then exits the biooxidation reactor. A definition of variable names and symbols used in the gas balance formulas is given in Table 1.1.

TABLE 1.1

Definition of Mathematical Variables and Symbols used in Component Gas Balance Calculations.

| Symbol | Exemplary units | Definition |
|---|---|---|
| $F_{air}$ | mgmoles/min | molar flowrate of air to the biooxidation reaction |
| $F_{O2}$ | mgmoles/min | molar flowrate of optional pure oxygen to the biooxidation reaction |
| $F_{out}$ | mgmoles/min | molar flowrate of gas leaving the bioxidation reaction |
| K | dimensionless | correction factor to gas measurement for an instrument calibrated with a gas other than the measured gas |
| P° | atm | standard pressure used by gas measurement instrument |
| R | atm liters/gmole K | gas law constant |
| $r_{CO2}$ | mgmole $CO_2$/ kg/hour | Rate of carbon dioxide production; CER |
| $-r_{O2}$ | mgmole $O_2$/ kg/hour | Rate of oxygen consumption; OUR |
| T° | K | Standard temperature used by gas measurement instrument |
| $V_{air}$ | std. liters/min | Volumetric flowrate of air at standard conditions |
| $V_{O2}$ | std. liters/min | Volumetric flowrate of oxygen at standard conditions |
| $V_f$ | kg | biooxidation reaction mass |
| $X_{N2air}$ | mole/mole | mole fraction nitrogen in compressor air |
| $X_{N2out}$ | mole/mole | mole fraction nitrogen in biooxidation offgas |
| $X_{O2air}$ | mole/mole | mole fraction oxygen in compressor air |
| $X_{O2out}$ | mole/mole | mole fraction oxygen in biooxidation offgas |
| $X_{CO2air}$ | mole/mole | mole fraction carbon dioxide in the compressor air |
| $X_{CO2out}$ | mole/mole | mole fraction carbon dioxide in biooxidation offgas |

Under steady flow conditions, the accumulation of nitrogen, carbon dioxide, and oxygen in the reaction mixture are considered negligible. Reactions of carbon dioxide to bicarbonates or carbonates are also negligible in the carbon dioxide balance except at extremely alkaline conditions (pH>8.5). Nitrogen is assumed not to react in the biooxidation reaction and is used as a tie component to link the gas flow measurement at the inlet to the gas flow at the exit. An alternative tie component is argon. This use of the tie component eliminates the need for an independent flow measurement at the outlet. The component gas balances for nitrogen, oxygen, and carbon dioxide are given by $$F_{air}(X_{N2air}) + F_{O2}(0) - F_{out}(X_{N2out}) = 0 \quad \text{Equation 1.1}$$

$$F_{air}(X_{O2air}) + F_{O2}(1) - F_{out}(X_{O2out}) + r_{O2}V_f = 0 \quad \text{Equation 1.2}$$

$$F_{in}(X_{CO2air}) + F_{O2}(0) - F_{out}(X_{CO2out}) + r_{CO2}V_f = 0 \quad \text{Equation 1.3}$$

It is clear then that the gas flow rate at the exit is related to the gas flow rate at the inlet by tie component nitrogen using Equation 1.1 by $$F_{out} = F_{air}(X_{N2air}/X_{N2out}) \quad \text{Equation 1.4}$$

Gas flow rates measurements are not usually expressed in molar flow rates, rather they are typically measured in volumetric terms. The molar gas flow rate is then related to the volumetric flow rate according to an equation of state. Under most flow conditions of biooxidation reactions the ideal gas law should suffice for the purpose of the component gas balance calculation. Alternative equations of state include, for example, the Van der Waals equation or Redlich- Kwong equation. Then the ideal gas law gives the molar flow rate of air and supplemental oxygen entering the biooxidation reactor $$F_{air} = \left(\frac{KP°}{RT°}\right)_{air\ flowmeter} V_{air} \qquad \text{Equation 1.5}$$

$$F_{O2} = \left(\frac{KP°}{RT°}\right)_{O2\ flowmeter} V_{O2} \qquad \text{Equation 1.6}$$

It should be understood that the terms T° and P° are evaluated at the flow conditions of V measurement. If the measurement of V is reported as a standard volumetric flow rate, then the terms T° and P° are the standard reference conditions of the measurement device. The term K is a correction applied when the measurement device is calibrated with a gas composition other than the gas being measured in the biooxidation reaction.

Substituting Equations 1.4, 1.5, and 1.6 into Equation 1.2 gives for the rate of oxygen consumption $$-r_{O2} \cdot V_f = \left(\frac{KP°}{RT°}\right)_{O2\ flowmeter} V_{O2} + \qquad \text{Equation 1.7}$$

$$\left(\frac{KP°}{RT°}\right)_{air\ flowmeter} V_{air}[X_{O2air} - X_{O2out}(X_{N2air}/X_{N2out})]$$

Similarly, substituting Equations 1.4 and 1.5 into Equation 1.3 gives for the rate of carbon dioxide evolution.

$$r_{CO2} \cdot V_f = \qquad \text{Equation 1.8}$$

$$\left(\frac{KP°}{RT°}\right)_{air\ flowmeter} V_{air}[X_{CO2out}(X_{N2air}/X_{N2out}) - X_{CO2air}]$$

These equations 1.7 and 1.8 together are useful intermediate derived variables used in executing the methods of this invention. If supplemental oxygen is not used then the term $V_{O2}=0$ in Equation 1.7.

EXAMPLE 2

Component Gas Balances Measurement Devices

Gas flow measurements may be made using any of a number of gas flow devices that generate a calibrated analog or digital signal representing the gas flow rate. These include thermal mass flow meters, orifice plate meters, and coriolus effect meters. These instruments typically express gas flow rates in standard volumetric units, that is the volumetric rate at some standard temperature and pressure. These are the standard T° and P° to be used in the method of Example 1. The instrument vendor can also supply the value for K if the gas flow instrument is used with a gas other than the calibration gas.

A variety of instruments can be used for the gas composition analysis in the method of Example 1. In that a common air supply might serve multiple biooxidation reactors, it is most useful to sample the compressor air supply and the biooxidations in a repeating sequence to a common instrument. Mass spectrometers are preferred measurement devices for their ability to simultaneous determine the mole or volume fraction of gas components in a scan of the gas sample, and for other reasons as previously described (Coppella and Dhurjati, 1987). Satisfactory performance was achieved using variable and fixed-sector mass spectrometers.

EXAMPLE 3

Operating and Stoichiometric Parameters for Combustion of Pure Co-Substrates This example relates to the determination of the stoichiometric coefficients of Reaction 2 for the combustion of pure co-substrate feeds (Xc=1). These coefficients are then used directly in the monitoring and control formulas of this invention.

Reaction 2 represents the net of a series of biochemical reactions by which energy is generated from co-substrate by the biocatalyst. It is not necessary that the pathway be known in determining the proper stoichiometric coefficients of Reaction 2, for the stoichiometry is the same for the complete combustion of the same co-substrate in the presence of oxygen to carbon dioxide and water. That is, for a co-substrate of chemical formula $C_xH_yO_z$, then the combustion stoichiometry is given as Reaction 3.1

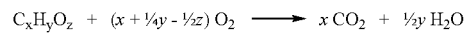

$$C_xH_yO_z + (x + \tfrac{1}{4}y - \tfrac{1}{2}z) O_2 \longrightarrow x\,CO_2 + \tfrac{1}{2}y\,H_2O$$

By inspection with Reaction 2 of the specification, then $$c_2 = 1 \qquad \text{Equation 3.1}$$

$$b_2 = (x + \tfrac{1}{2}y - \tfrac{1}{2}z) \qquad \text{Equation 3.2}$$

$$e_2 = x \qquad \text{Equation 3.3}$$

$$f_2 = \tfrac{1}{2}y \qquad \text{Equation 3.4}$$

It is also clear that $$Mw_C = 12.011x + 1.008y + 15.999z \qquad \text{Equation 3.5}$$

Further for use of a pure component co-substrate then $$Xc = 1 \qquad \text{Equation 3.6}$$

These relationships, Equations 3.1-3.6, define certain of the operating line and stoichiometric parameters used in the monitoring and control strategy according to the invention. They have been applied to a number of exemplary pure co-substrates that can be used with the methods of this invention as shown in Table 3.1.

TABLE 3.1

Example Biooxidation Co-substrates and Parameters Related to Co-substrate Combustion Reaction 2.

| Parameter[1] | Operating Line Parameters | | | Stoichiometric Parameters | | | |
|---|---|---|---|---|---|---|---|
| | $Mw_C$ | $X_C$ | $(Mw_C/X_C)$ | $c_2$ | $b_2$ | $e_2$ | $f_2$ |
| Co-substrate Organic Acids | | | | | | | |
| Formic Acid | 46.03 | 1.0 | 46.03 | 1 | 0.5 | 1 | 1 |
| Acetic Acid | 60.05 | 1.0 | 60.05 | 1 | 2 | 2 | 2 |
| Propionic Acid | 74.08 | 1.0 | 74.08 | 1 | 3.5 | 3 | 3 |

TABLE 3.1-continued

Example Biooxidation Co-substrates and Parameters
Related to Co-substrate Combustion Reaction 2.

| Parameter[1] | Operating Line Parameters | | | Stoichiometric Parameters | | | |
|---|---|---|---|---|---|---|---|
| | $Mw_C$ | $X_C$ | $(Mw_C/X_C)$ | $c_2$ | $b_2$ | $e_2$ | $f_2$ |
| Lactic Acid | 90.08 | 1.0 | 90.08 | 1 | 3 | 3 | 3 |
| Lauric Acid | 200.31 | 1.0 | 200.31 | 1 | 17 | 12 | 12 |
| Myristic Acid | 228.36 | 1.0 | 228.36 | 1 | 20 | 14 | 14 |
| Myristoleic Acid | 226.36 | 1.0 | 226.36 | 1 | 19.5 | 14 | 13 |
| Palmitic Acid | 256.42 | 1.0 | 256.42 | 1 | 23 | 16 | 16 |
| Palmitoleic Acid | 254.41 | 1.0 | 254.41 | 1 | 22.5 | 16 | 15 |
| Margaric Acid | 270.45 | 1.0 | 270.45 | 1 | 24.5 | 17 | 17 |
| Stearic Acid | 284.47 | 1.0 | 284.47 | 1 | 26 | 18 | 18 |
| Oleic Acid | 282.45 | 1.0 | 282.45 | 1 | 25.5 | 18 | 17 |
| Linoleic Acid | 280.44 | 1.0 | 280.44 | 1 | 25 | 18 | 16 |
| Linolenic Acid | 278.43 | 1.0 | 278.43 | 1 | 24.5 | 18 | 15 |
| Alcohols | | | | | | | |
| Methanol | 32.04 | 1.0 | 32.04 | 1 | 1.5 | 1 | 2 |
| Ethanol | 46.07 | 1.0 | 46.07 | 1 | 3 | 2 | 3 |
| Glycerol | 92.09 | 1.0 | 92.09 | 1 | 3.5 | 3 | 4 |
| Carbohydrates | | | | | | | |
| Glucose | 180.16 | 1.0 | 180.16 | 1 | 6 | 6 | 6 |
| Fructose | 180.16 | 1.0 | 180.16 | 1 | 6 | 6 | 6 |
| Maltose | 342.30 | 1.0 | 342.30 | 1 | 12 | 12 | 11 |
| Sucrose | 342.30 | 1.0 | 342.30 | 1 | 12 | 12 | 11 |
| Lactose | 342.30 | 1.0 | 342.30 | 1 | 12 | 12 | 11 |
| Hydrocarbons | | | | | | | |
| Methane | 16.04 | 1.0 | 16.04 | 1 | 2 | 1 | 2 |
| Ethane | 30.07 | 1.0 | 30.07 | 1 | 3.5 | 2 | 3 |
| Propane | 44.09 | 1.0 | 44.09 | 1 | 5 | 3 | 4 |
| Butane | 58.12 | 1.0 | 58.12 | 1 | 6.5 | 4 | 5 |
| Pentane | 72.15 | 1.0 | 72.15 | 1 | 8 | 5 | 6 |
| Hexane | 86.17 | 1.0 | 86.17 | 1 | 9.5 | 6 | 7 |
| Octane | 114.22 | 1.0 | 114.22 | 1 | 12.5 | 8 | 9 |
| Iso-octane | 114.22 | 1.0 | 114.22 | 1 | 12.5 | 8 | 9 |
| Decane | 142.28 | 1.0 | 142.28 | 1 | 15.5 | 10 | 11 |
| Dodecane | 170.33 | 1.0 | 170.33 | 1 | 18.5 | 12 | 13 |
| Tridecane | 184.36 | 1.0 | 184.36 | 1 | 20 | 13 | 14 |
| Tetradecane | 198.38 | 1.0 | 198.38 | 1 | 21.5 | 14 | 15 |
| Hexadecane | 226.43 | 1.0 | 226.43 | 1 | 24.5 | 16 | 17 |

[1]Definition and exemplary units are given in Table 1.

EXAMPLE 4

Operating and Stoichiometric Parameters for Combustion of Co-Substrate Mixtures

This example relates to the use of co-substrate where the co-substrate is a mixture of metabolized and unmetabolized components.

There is a strong economic incentive to use technical or commercial forms of chemicals as co-substrates due to the high cost and availability of pure compounds. Co-substrates selected from the basic chemicals of the agrochemical and petrochemical industries will then comprise a mixture of metabolized and unmetabolized components. Also processing aids may be added during the preparation of the ultimate co-substrate stream fed to the biooxidation reaction. These need to be accounted for in determining the appropriate values for the operating and stoichiometric parameters of this invention. If the co-substrate consists only of metabolized substances and a molecular formula is available for the mixture then it is possible to use the method of Example 2 in determining the stoichiometric and certain operating parameters.

If the co-substrate consists of i components, of which j of the components are metabolized, then the operating parameters are given by $$X_C = \sum_j X_{Ci} \qquad \text{Equation 4.1}$$

and $$Mw_C = \frac{X_C}{\sum_j (X_{Ci}/Mw_{Ci})} \qquad \text{Equation 4.2}$$

For calculating the stoichiometric parameters it is useful to first convert the mass fractions to mole fractions of metabolizable components, then $$Z_{Ci} = \frac{(X_{Ci}/Mw_{Ci})}{\sum_j (X_{Ci}/Mw_{Ci})} \qquad \text{Equation 4.3}$$

Then each of the stoichiometric parameters is determined from the stoichiometric parameters for each of the individual pure components using the methods of Example 3 according to $$c_2 = \sum_j (c_{2i} \cdot Z_{Ci}) \qquad \text{Equation 4.4}$$

$$b_2 = \sum_j (b_{2i} \cdot Z_{Ci}) \qquad \text{Equation 4.5}$$

$$e_2 = \sum_j (e_{2i} \cdot Z_{Ci}) \qquad \text{Equation 4.6}$$

$$f_2 = \sum_j (f_{2i} \cdot Z_{Ci}) \qquad \text{Equation 4.7}$$

Implementing these mixture rules is readily achieved in a spreadsheet software program.

EXAMPLE 5

Preparation of Glucose Co-Substrate Feed

A 50.5% glucose feed was prepared for use in an untempered feed system by dissolving 1497 kg of glucose monohydrate into 1198 kg of water. The aqueous solution was then transferred to a pressure vessel and sterilized by indirect steam heating. This feed (2695 kg) then contained 1361 kg glucose, 136 kg water of hydration, and 1198 kg of solvent water.

The relevant sums of Equations 4.1-4.7 are calculated for use in determining the operating and stoichiometric parameters for using this feed as co-substrate as shown in Table 5.1.

TABLE 5.1

Calculation of Operating and Stoichiometric Parameters for use of a Glucose Co-substrate Feed Prepared from Dextrose Monohydrate.

|  | $Mw_{Ci}$ | $X_{Ci}$ | $X_{Ci}/Mw_{Ci}$ | $Z_{Ci}$ | $c_{2i} \cdot Z_{Ci}$ | $b_{2i} \cdot Z_{Ci}$ | $e_{2i} \cdot Z_{Ci}$ | $f_{2i} \cdot Z_{Ci}$ |
|---|---|---|---|---|---|---|---|---|
| Metabolized Components | | | | | | | | |
| Glucose | 180.16 | 0.505 | 0.002803 | 1 | 1 | 6 | 6 | 6 |
| Subtotal metabolized | | | 0.002803 | 1 | 1 | 6 | 6 | 6 |
| Unmetabolized Components | | | | | | | | |
| Water of Hydration | | 0.050 | | | | | | |
| Solvent Water | | 0.445 | | | | | | |
| Subtotal unmetabolized | | 0.495 | | | | | | |
| Total | | 1.000 | | | | | | |
| Calculation Results: | | | | | | | | |
| Operating Parameter | | $Mw_C$ | 180.16 | | Equation 4.1 | | | |
| Operating Parameter | | $X_C$ | 0.505 | | Equation 4.2 | | | |
| Stoichiometric Parameter | | $c_2$ | 1 | | Equation 4.4 | | | |
| Stoichiometric Parameter | | $b_2$ | 6 | | Equation 4.5 | | | |
| Stoichiometric Parameter | | $e_2$ | 6 | | Equation 4.6 | | | |
| Stoichiometric Parameter | | $f_2$ | 6 | | Equation 4.7 | | | |

EXAMPLE 6

Preparation of a Glucose Co-Substrate Feed

Alternatively, a glucose co-substrate feed was prepared from commercial 95DE Corn Syrup containing 72% dry solids. The dry solids fraction is comprised of 96% metabolizable glucose and the remaining 4% solids were considered unmetabolized. Bulk shipments of 95 DE Corn Syrup were diluted with water to 55% dry solids for convenient use in an un-tempered storage and distribution system.

A measured aliquot of diluted corn syrup was transferred to a storage tank for sterilization and feeding a biooxidation reaction. Prior to use the tank and diluted corn syrup were sterilized by direct steam heating which further diluted the corn syrup due to the accumulation of steam condensate. The final dry solids content of the resulting co-substrate feed was 47.1% dry solids.

The solids content in the corn syrup and intermediate streams in preparing this co-substrate feed were conveniently determined by correlation with refractive index measurements.

By simultaneous solution of overall and component material balances around the dilution and sterilization operations, a basis 1000 kg of the final sterile co-substrate feed then contained: 452.2 kg glucose, 18.8 kg other solids, 143.6 kg steam condensate, 202.2 kg dilution water, and 183.2 kg water from the corn syrup. The relevant sums of Equations 4.1-4.7 are calculated for use in determining the operating and stoichiometric parameters for the use of this feed as co-substrate as shown in Table 6.1.

TABLE 6.1

Calculation of Operating and Stoichiometric Parameters for use of a Glucose Co-substrate Feed Prepared from 95 DE Corn Syrup.

|  | $Mw_{Ci}$ | $X_{Ci}$ | $X_{Ci}/Mw_{Ci}$ | $Z_{Ci}$ | $c_{2i} \cdot Z_{Ci}$ | $b_{2i} \cdot Z_{Ci}$ | $e_{2i} \cdot Z_{Ci}$ | $f_{2i} \cdot Z_{Ci}$ |
|---|---|---|---|---|---|---|---|---|
| Metabolized Components | | | | | | | | |
| Glucose | 180.16 | 0.452 | 0.00251 | 1 | 1 | 6 | 6 | 6 |
| Subtotal metabolized | | 0.452 | 0.00251 | 1 | 1 | 6 | 6 | 6 |
| Unmetabolized Components | | | | | | | | |
| Water from Corn Syrup | | 0.183 | | | | | | |
| Dilution Water | | 0.202 | | | | | | |
| Other Corn Syrup solids | | 0.019 | | | | | | |
| Steam Condensate | | 0.144 | | | | | | |
| Subtotal unmetabolized | | 0.548 | | | | | | |
| Total | | 1.000 | | | | | | |
| Calculation Results | | | | | | | | |
| Operating Parameter | | $Mw_C$ | 180.16 | | Equation 4.1 | | | |
| Operating Parameter | | $X_C$ | 0.452 | | Equation 4.2 | | | |
| Stoichiometric Parameter | | $c_2$ | 1 | | Equation 4.4 | | | |
| Stoichiometric Parameter | | $b_2$ | 6 | | Equation 4.5 | | | |

TABLE 6.1-continued

Calculation of Operating and Stoichiometric Parameters for use of a Glucose Co-substrate Feed Prepared from 95 DE Corn Syrup.

| | $Mw_{Ci}$ | $X_{Ci}$ | $X_{Ci}/Mw_{Ci}$ | $Z_{Ci}$ | $c_{2i} \cdot Z_{Ci}$ | $b_{2i} \cdot Z_{Ci}$ | $e_{2i} \cdot Z_{Ci}$ | $f_{2i} \cdot Z_{Ci}$ |
|---|---|---|---|---|---|---|---|---|
| Stoichiometric Parameter | | $e_2$ | 6 | | | Equation 4.6 | | |
| Stoichiometric Parameter | | $f_2$ | 6 | | | Equation 4.7 | | |

EXAMPLE 7

Preparation of a Mixed-Sugar Co-Substrate Feed

Specifications for a STALEYDEX® 95 M Liquid Dextrose show it to contain 71%-72% dry substance of which 95% (min) is monosaccharides, 86% (min) is glucose and 9% (max) is fructose. An HPLC analysis of the STALEYDEX® 95 M Liquid Dextrose confirmed its glucose content was 61.3% glucose. The fructose, taken as 9% of the dry matter, was found to be similarly metabolized in parallel with glucose in a biooxidation reaction. Fructose was therefore included as a metabolized component.

A mixed sugar co-substrate feed to contain 50% glucose was prepared by mixing 2.26 kg deionized water to 10 kg STALEYDEX® 95 M Liquid Dextrose. The dilution was for ease of handling in an un-tempered laboratory biooxidation system. This final co-substrate solution (12.26 kg) was then comprised of 6.13 kg glucose, 0.635 kg fructose, 0.285 kg other solids, 2.95 kg water from the liquid dextrose, and 2.26 kg dilution water. The mixture was distributed to canning jars, sealed according to the manufacturers recommendation, then autoclaved in a laboratory autoclave for later use. The relevant sums of Equations 4.1-4.7 are calculated for use in determining the operating and stoichiometric parameters for the use of this feed as co-substrate as shown in Table 7.1.

EXAMPLE 8

Preparation of a Fatty Acid Co-Substrate Feed

Two hundred grams of EMERSOL® Oleic Acid having typical composition given in Table 8.1 was charged to an Erlenmeyer flask. Prior to sterilization by indirect steam heating, 10 grams of distilled water was added to improve the effectiveness of sterilization. The post sterilization co-substrate therefore contained 95.2% EMERSOL® Oleic Acid and 4.8% water.

TABLE 8.1

Typical Composition of EMERSOL ® Oleic Acid.

| Component Fatty Acid | weight % |
|---|---|
| Myristic Acid | 3 |
| Myristoleic Acid | 3 |
| Palmitic Acid | 4 |
| Palmitoleic Acid | 7 |
| Margaric Acid | 1 |
| Oleic Acid | 73 |
| Linoleic Acid | 8 |
| Linolenic Acid | 1 |

TABLE 7.1

Calculation of Operating and Stoichiometric Parameters for use of a Mixed-Sugar Co-substrate Feed Prepared from STALEYDEX 95M Liquid Dextrose.

| | $Mw_{Ci}$ | $X_{Ci}$ | $X_{Ci}/Mw_{Ci}$ | $Z_{Ci}$ | $c_{2i} \cdot Z_{Ci}$ | $b_{2i} \cdot Z_{Ci}$ | $e_{2i} \cdot Z_{Ci}$ | $f_{2i} \cdot Z_{Ci}$ |
|---|---|---|---|---|---|---|---|---|
| Metabolized Components | | | | | | | | |
| Fructose | 180.16 | 0.052 | 2.87E−4 | 0.906 | 0.906 | 5.437 | 5.437 | 5.437 |
| Glucose | 180.16 | 0.500 | 0.00278 | 0.094 | 0.094 | 0.563 | 0.563 | 0.563 |
| Subtotal metabolized | | 0.552 | 0.00251 | 1 | 1 | 6 | 6 | 6 |
| Unmetabolized Components | | | | | | | | |
| Water from Liquid Dextrose | | 0.241 | | | | | | |
| Dilution Water | | 0.184 | | | | | | |
| Other Liquid Dextrose solids | | 0.023 | | | | | | |
| Subtotal unmetabolized | | 0.448 | | | | | | |
| Total | | 1.000 | | | | | | |
| Calculation Results | | | | | | | | |
| Operating Parameter | | $Mw_C$ | 180.16 | | | Equation 4.1 | | |
| Operating Parameter | | $X_C$ | 0.552 | | | Equation 4.2 | | |
| Stoichiometric Parameter | | $c_2$ | 1 | | | Equation 4.4 | | |
| Stoichiometric Parameter | | $b_2$ | 6 | | | Equation 4.5 | | |
| Stoichiometric Parameter | | $e_2$ | 6 | | | Equation 4.6 | | |
| Stoichiometric Parameter | | $f_2$ | 6 | | | Equation 4.7 | | |

The relevant sums of Equations 4.1-4.7 are calculated for use in determining the operating and stoichiometric parameters for the use of this feed as co-substrate as shown in Table 8.2. A similar approach is used for the many fatty acids of commerce.

The most frequent situation however, is that sufficient information is indeed available in the literature to at least write a plausible stoichiometry, but conflicting information exists or information is missing leaving uncertainty in the overall reaction stoichiometry.

TABLE 8.2

Calculation of Operating and Stoichiometric Parameters for use of a Mixed-Fatty Acid Co-substrate Feed Prepared from EMERSOL ® Oleic Acid.

| | $Mw_{Ci}$ | $X_{Ci}$ | $X_{Ci}/Mw_{Ci}$ | $Z_{Ci}$ | $C_{2i} \cdot Z_{Ci}$ | $b_{2i} \cdot Z_{Ci}$ | $e_{2i} \cdot Z_{Ci}$ | $f_{2i} \cdot Z_{Ci}$ |
|---|---|---|---|---|---|---|---|---|
| Metabolized Components | | | | | | | | |
| Myristic Acid | 228.36 | 0.029 | 0.00013 | 0.036 | 0.036 | 0.722 | 0.506 | 0.506 |
| Myristoleic Acid | 226.36 | 0.029 | 0.00013 | 0.036 | 0.036 | 0.710 | 0.510 | 0.474 |
| Palmitic Acid | 256.42 | 0.038 | 0.00015 | 0.043 | 0.043 | 0.986 | 0.686 | 0.686 |
| Palmitoleic Acid | 254.40 | 0.067 | 0.00026 | 0.076 | 0.076 | 1.702 | 1.210 | 1.135 |
| Margaric Acid | 270.45 | 0.010 | 0.00004 | 0.010 | 0.010 | 0.249 | 0.173 | 0.173 |
| Oleic Acid | 282.45 | 0.695 | 0.00246 | 0.710 | 0.710 | 18.117 | 12.789 | 12.078 |
| Linoleic Acid | 280.44 | 0.076 | 0.00027 | 0.078 | 0.078 | 1.960 | 1.412 | 1.255 |
| Linolenic Acid | 278.43 | 0.010 | 0.00003 | 0.010 | 0.010 | 0.242 | 0.178 | 0.148 |
| Subtotal metabolized | | 0.952 | 0.00346 | 1 | 1 | 24.69 | 17.46 | 16.45 |
| Unmetabolized Components | | | | | | | | |
| Water (sterilization aid) | | 0.048 | | | | | | |
| Subtotal unmetabolized | | 0.448 | | | | | | |
| Total | | 1.000 | | | | | | |
| Calculation Results | | | | | | | | |
| Operating Parameter | $Mw_C$ | 274.9 | | Equation 4.1 | | | | |
| Operating Parameter | $X_C$ | 0.952 | | Equation 4.2 | | | | |
| Stoichiometric Parameter | $c_2$ | 1 | | Equation 4.4 | | | | |
| Stoichiometric Parameter | $b_2$ | 24.69 | | Equation 4.5 | | | | |
| Stoichiometric Parameter | $e_2$ | 17.46 | | Equation 4.6 | | | | |
| Stoichiometric Parameter | $f_2$ | 16.45 | | Equation 4.7 | | | | |

EXAMPLE 9

Summary of Approaches for Establishing the Stoichiometric and Operating Parameters for Biooxidation Substrates In contrast to the methods used for establishing stoichiometric and operating parameters for the co-substrate which relied on co-substrate combustion stoichiometry, the diversity of potential biooxidation substrates and biooxidation products does not lend itself immediately to such simple rules. The path taken in oxidizing the substrate to ultimate desired product contains at least one step involving molecular oxygen, but may well contain more than one. The path may include additional steps not directly involving molecular oxygen.

In cases where the pathway from substrate to product is known, and the stoichiometry of each step is known, then one can determine the overall reaction stoichiometry. This may well be the case for a biocatalyst deliberately created using recombinant DNA techniques.

In recent years there has been much scientific study on the enzyme and enzyme systems that use molecular oxygen. There may be sufficient information available in the open literature for a similar biooxidation reaction to write a priori the correct overall reaction stoichiometry for the desired oxidation.

EXAMPLE 10

Figure 2:
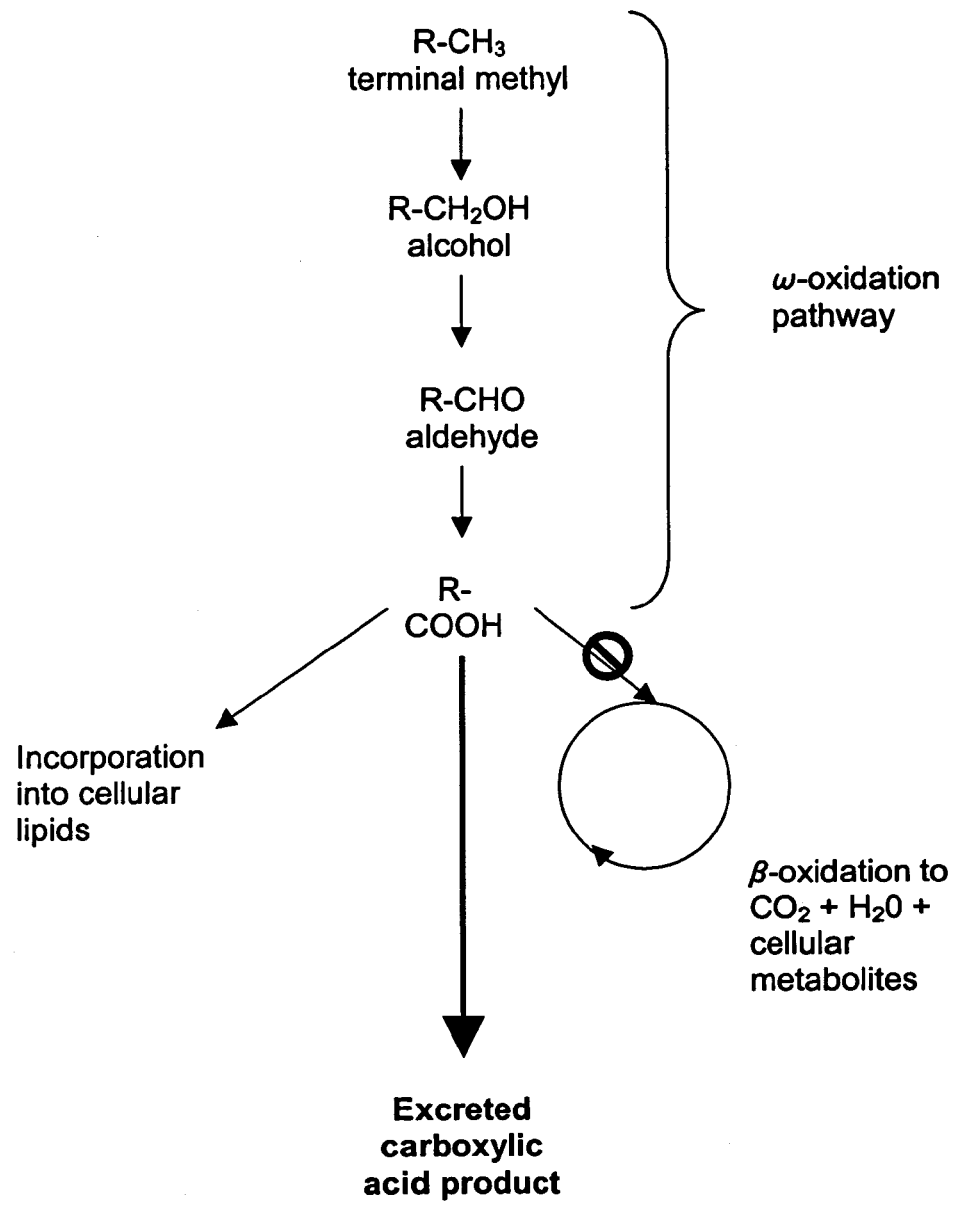
FIG. 2 shows the ω-oxidation pathway and its relationship to other metabolic pathway.

Oxidation of Alkanes and Fatty Acids to Dicarboxylic Acids: Determining Substrate Stoichiometric Parameters from Literature Data The mechanism by which alkanes enter metabolic degradation pathways is generally regarded to occur through the sequential oxidation of a terminal methyl carbon: first to an alcohol, then the aldehyde, and finally to a carboxylic acid. This pathway oxidizing the terminal methyl carbon to carboxylic acid is termed the ω-oxidation pathway. The resulting fatty acid then can enter the β-oxidation pathway for further degradation or can be incorporation into the pool of cellular lipids. Rehm and Reiff (Adv. Biochem. Eng., 9, pgs. 175-215, 1981) reviewed the various mechanisms for oxidation of alkanes in microorganisms. FIG. 2 schematically shows the ω-oxidation pathway and its relationship to β-oxidation oxidation and fatty acid incorporation.

It has been demonstrated in *Candida tropicalis* that, if the β-oxidation pathway is blocked, then alkane and fatty acid substrates are converted to their corresponding dicarboxylic acids in high purity and high yield (Picataggio et al, Bio/technology, pp 894-898 1992 and U.S. Pat. No. 5,254,466). Thus the substrate carbon is directed to the omega oxidation pathway to be excreted from the cell. Fermentation procedures involved growing a population of cells then feeding a glucose co-substrate at a prescribed rate. Substrate was added based on periodic sampling and offline analysis to maintain a residual substrate concentration at 4-60 grams/liter of fermentation broth.

To apply the methods of this invention to the biooxidation process of Picataggio, it is first useful to assess what is known about the overall stoichiometry of the ω-oxidation reaction, particularly in yeast, and in particularly *Candida tropicalis*. Gallo et al ("Alkane Oxidation in *Candida tropicalis*", Biochimica et Biophysical Acta,. 296, pgs. 624-638, 1973) confirmed and extended prior work that the first NADPH-dependent hydroxylation step mediated by the mixed function monooxygenase cytochrome P450. Rehm and Reiff (loc cit) gave the stoichiometry for this hydroxylation reaction as shown in FIG. 3.

Early work of Gallo et al (loc cit) suggested that the second step to oxidize the alcohol to an aldehyde was catalyzed by an $NAD^+$-dependent dehydrogenase not involving the molecular oxygen. Later work by Kemp et al (Appl. Microbiol. Biotechnol, 29, pgs. 370-374, 1988) contradicted that work and demonstrated that the reaction was catalyzed by an alcohol oxidase involving the consumption of oxygen and liberation of hydrogen peroxide as shown in FIG. 3.

Hydrogen peroxide is a reactive species unlikely to accumulate in the cell. It is noteworthy that the aldehyde and hydrogen peroxide could spontaneously react to form a carboxylic acid and water. Rather it is more likely that the enzyme catalase disposes of this reactive species to give oxygen and water as shown in FIG. 3.

Finally, the work of both Gallo et al (loc cit) and Kemp et al (loc cit) agree that the final step is catalyzed by an $NAD^+$-dependent dehydrogenase to yield the carboxylic acid.

A plausible reaction scheme for the oxidation of terminal methyl groups, especially related to dicarboxylic acid formation from alkanes and fatty acids is given as the net ω-oxidation reaction of FIG. 3. When applied to a fatty acid substrate, one pass is needed through this reaction consuming 1.5 moles of oxygen and yielding one mole of product. When applied to an alkane substrate, two passes are needed to oxidize each end of the alkane to a dicarboxylic acid consuming 3 moles of oxygen for every mole of substrate and product.

Uncertainty in the stoichiometry arises in that some alcohol dehydrogenase activity could potentially exist in parallel with the oxidase activity. Also some spontaneous reaction of the hydrogen peroxide with the aldehyde, both products of the alcohol oxidase, might occur in vivo. Additionally, recent work with cytochrome P450 from *Candida maltosa* (Scheller et al, "Oxygenation Cascade in Conversion of n-Alkanes to α,ω-Dioic Acids Catalyzed by Cytochrome P450 52A3", J of Biological Chemistry, 273, pgs. 32528-32534, 1998) and *C. tropicalis* (Eschenfeldt et al., "Transformation of Fatty Acids Catalyzed by Cytochrome P450 Monooxygenase Enzymes of *Candida tropicalis*", Applied and Environmental Microbiol., 69, pgs. 5992-5999, 2003) have demonstrated in vitro that this enzyme can catalyze all the reactions of the ω-oxidation pathway. This would give the carboxylic acid with the incumbent consumption of three moles of oxygen for each pass through the pathway.

EXAMPLE 11

Alternative Expression of Biooxidation Rate and Control Equations

In the preferred embodiment of this invention rates of substrate and co-substrate consumption are determined from the component gas balances (the stoichiometric line). Proportional adjustments are made to the substrate and co-substrate feed rates (the operating line).

It has been found that an alternative can readily be applied for those who seek to test the methods of this invention which is identical to the preferred embodiment for a wide range of biooxidation reactions.

This alternative method makes use of the same system of simultaneous reactions 1-5 already described herein. In this analysis however, the following simplifications and definitions are made:

1) The rate of Reaction 4 is assumed to be zero or is temporarily, for experimental purpose, made to be zero, that is $\Psi=0$.
2) The rates of Reactions 1 and 2 are defined in terms of oxygen consumption and carbon dioxide evolution, respectively.
3) The stoichiometric coefficient on co-substrate in Reaction 1 is assumed to be 0 or is temporarily, for experimental purpose, made to be zero, that is $c_1=0$.

According to the stoichiometry of Reaction 1, then the rate of reaction 1 may be expressed in terms of oxygen consumption as $$r_{1a} = (b_1/a_1)r_1 \qquad \text{Equation 12}$$

Similarly, from the stoichiometry of reaction 2, the rate of reaction 2 may be expressed in terms of carbon dioxide evolution as $$r_{2a} = -(e_2/c_2)r_2 \qquad \text{Equation 13}$$

Substituting Equation 7 into equation 12 subject to the foregoing assumptions gives $$r_{1a} = \frac{-r_{O2} - (b_2/e_2)r_{CO2}}{1-(b_2/e_2)(e_1/b_1)}. \qquad \text{Equation 14}$$

This Equation 14 gives the rate of substrate oxidation in terms of oxygen consumption by Reaction 1.

Similarly, substituting Equation 7 and 4 into Equation 13 subject to the forgoing assumptions gives the rate of co-substrate combustion in terms of carbon dioxide evolution.

$$r_{2a} = \frac{-r_{CO2} - (e_1/b_1)r_{O2}}{1-(b_2/e_2)(e_1/b_1)}. \qquad \text{Equation 15}$$

The resulting simultaneous reactions for the oxidation of substrate and combustion of co-substrate indeed do describe a wide range of potential biooxidation reactions. This alternative form is also useful for independently measuring the reaction stoichiometry when the reaction stoichiometry is not known or is uncertain.

A plot of $r_{2a}$ and $r_{1a}$ using Equations 15 and 14 respectively versus time over the course of the fermentation establishes the equilibrium lines for the fermentation.

It is now possible to establish the substrate and co-substrate operating lines in terms of the expected oxygen consumption by oxidation of the substrate and an expected carbon dioxide evolution by combustion of the co-substrate, respectively.

Then for oxidation of the substrate, $$F_s \text{setpoint} = 0.001\, A_3(a_1/b_1)(Mw_s/X_s)(-r_{1a})V_f \qquad \text{Equation 16}$$

The substrate operating line is then defined by a plot of $-r_{1a}$ (theoretical) during the course of the biooxidation according to Equation 17.

$$-r_{1a}(\text{theoretical}) = F_s(b_1/a_1)\frac{X_s Mw_s}{V_f} \quad \text{Equation 17}$$

Similarly, for the co-substrate, $$F_c \text{setpoint} = 0.001 A_4(c_2/e_2)(Mw_c/X_c)(-r_{2a})V_f \quad \text{Equation 18}$$

The co-substrate operating line is then defined by a plot of $-r_{2a}$ (theoretical) during the course of the biooxidation according to Equation 17.

$$-r_{2a}(\text{theoretical}) = F_c(e_2/c_2)\frac{X_c Mw_c}{V_f} \quad \text{Equation 19}$$

Despite the earlier assumptions, this alternative method could be satisfactorily used for control purposes even when the co-substrate is consumed in reaction 1 and when some biomass accumulation is desirable (Reaction 4) simply by practicing the methods of this invention using operating values of $A_4$ greater than 1.

We have found this method to give satisfactory biooxidation results in facilities where not all the comparator and control formulas are programmed on a computer, but where only OUR and CER are given as derived variables. These simplified control calculations are easily done using a hand held calculator. The inventors have applied these calculations in laboratory to large pilot-scale bio-oxidation reactions.

EXAMPLE 12

Oxidation of an Oleic Acid Substrate to 9-octadecenedioic Acid by ω-Oxidation: Preparing the Oleic Acid Substrate Feed About 1500 kg of an oleic acid substrate having the composition shown in Table 12.1 was added to a sterile feed tank. An average fatty acid molecular weight was determined from this composition and found to be 281.1 g/gmole using the method analogous to that of for the co-substrate.

A similar determination done by mass spectroscopy was found to give an empirical chemical formula for this fatty acid mixture of $C_{17.92}H_{33.86}O_2$ having an empirical formula weight of 281.4 g/gmole, which closely agrees with the calculation above. This formula may also be written to reflect the basic fatty acid structure as $CH_3C_{15.92}H_{29.86}COOH$, recalling the objective to oxidize the terminal methyl to a carboxyl via ω-oxidation.

This substrate feed contained no processing aids nor other unmetabolized components, therefore $X_s=1$.

The stoichiometric parameters for substrate oxidation Reaction 1, assuming the proposed ω-oxidation stoichiometry of Example 10 and FIG. 3 are correct then, for $a_1=1$, $b_1=1.5$; $c_1=0$ $d_1=1$, $e_1=0$, $f_1=1$.

TABLE 12.1

| Oleic acid Composition | |
|---|---|
| Component Fatty Acid | Weight % |
| Lauric Acid | 0.1 |
| Myristic Acid | 0.1 |
| Pentadecanoic Acid | 0.1 |
| Palmitic Acid | 3.8 |
| Palmitoleic Acid | 0.1 |
| Stearic Acid | 4.7 |
| Oleic Acid | 85 |
| Linoleic Acid | 5.2 |
| Linolenic Acid | 0.4 |
| Eicosenoic Acid | 0.3 |

EXAMPLE 13

Oxidation of an Oleic acid Substrate to 9-octadecenedioic acid by ω-Oxidation using a Glucose Co-Substrate: Setting up the Control Formulas Since uncertainty remains in the stoichiometry of the ω-oxidation it was first necessary to verify the reaction stoichiometry proposed in Example 10 and FIG. 3. To do this, a well-characterized glucose co-substrate feed was selected and its feed rate controlled according to the methods of this invention. Similarly, a well characterized oleic acid substrate was used though its feed rate was not controlled pending verification of reaction stoichiometry. Substrate operating and stoichiometric lines were constructed assuming the proposed ω-oxidation stoichiometry to be correct.

Thus the oleic acid feed of Example 12 was oxidized by a β-oxidation blocked *Candida tropicalis* H 5343 as described in U.S. Pat. No. 5,254,466, the entire contents of which are incorporated herein by reference, using the glucose feed of Example 5. The biooxidation was monitored using the method of Example 11 using the stoichiometric and operating parameters for these respective feeds.

The rate of biooxidation is given by substituting the parameters into Equation 14 to give $$r_{1a} \cdot V_f = \frac{-r_{O2} - (6/6)r_{CO2}}{1 - (6/6)(0/1.5)} \quad \text{Equation 13.1}$$
$$= (-r_{O2} - r_{CO2}) \cdot V_f$$
$$= (-OUR + CER) \cdot V_f$$

Similarly, for the rate of co-substrate combustion using Equation 15 gives $$r_{2a} \cdot V_f = \frac{-r_{CO2} - (0/1.5)r_{O2}}{1 - (6/6)(0/1.5)} \cdot V_f \quad \text{Equation 13.2}$$
$$= -r_{CO2} \cdot V_f = -CER \cdot V_f$$

Then the rate of the biooxidation reaction is determined for the difference in OUR and CER while the rate of co-substrate consumption is determined from the CER.

Substrate and co-substrate feed rate set points are determined by substituting the indicated operating and stoichiometric parameters into Equations 16 and 18 respectively.

$$F_s \text{set point} = 0.001\, A_3\, (1/1.5)(281.4/1.0)(OUR\text{-}CER)V_f \quad \text{Equation 13.3}$$

$$F_c \text{set point} = 0.001 A_4\, (1/6)(180.16/0.505)(CER)V_f \quad \text{Equation 13.4}$$

The operating line for the substrate feed is then given by substituting the appropriate stoichiometric and operating parameters into Equation 17.

$$-r_{1a}(\text{theoretical})\cdot V_f = F_s \cdot (1.5/1)\cdot 1.0\cdot (281) \quad \text{Equation 13.5}$$

This equation 13.5 relates the substrate feed rate $F_s$ to the same basis as used for the construction of the stoichiometric line. That is, it calculates what the expected oxygen consumption would be if all the oleic acid is converted to product according to the reaction stoichiometry. The actual feed rate may be greater, equal to, or less than the rate of reaction according to the value selected for $A_3$.

Similarly, the co-substrate operating line is given by substituting the appropriate stoichiometric and operating parameters into Equation 19

$$r_{2a}(\text{theoretical})\cdot V_f = F_c \cdot (6/1)\cdot 0.505\cdot 180 \quad \text{Equation 13.6}$$

This equation 13.6 relates the co-substrate feed rate $F_c$ to the same basis as used for the construction of the stoichiometric line. That is, it calculates what the expected carbon dioxide evolution would be if all the glucose is converted to product according to the combustion stoichiometry. The actual feed rate may be greater, equal to, or less than the rate of reaction according to the value selected for $A_4$.

The fermentation is then graphically represented two sets of plots. The first plot compares the rate of co-substrate combustion represented by the measured $CER\cdot V_f$ (stoichiometric line) and is compared with a theoretical $CER\cdot V_f$ calculated for the prevailing glucose feed rate $-r_{2a}$ (theoretical)$\cdot V_f$ (operating line). The second plot compares the rate of $\omega$-oxidation represented by $(OUR\text{-}CER)\cdot V_f$ (stoichiometric line) and is compared with a theoretical value $(OUR\text{-}CER)\cdot V_f$ calculated for the prevailing oleic acid feed rate r1a (theoretical)$\cdot V_f$ (operating line).

These formulas can be executed in an automatic feedback control loop. In practice, we have achieved successful results by simply monitoring the fermentation and making periodic feed rate adjustments.

EXAMPLE 14

Oxidation of an Oleic Acid Substrate to 9-octadecenedioic Acid by ω-Oxidation using a Glucose Co-Substrate A fermentor was charged with 9700 kg of synthetic growth medium as described in U.S. Pat. No. 6,569,670, the entire contents of which are incorporated herein by reference. The user defined fermentation volume was set to 1000 kg so that the CER and OUR data had units of gmoles/hr. The medium was inoculated with 300 kg of an actively growing culture of a β-oxidation blocked *Candida tropicalis* yeast of Example 13 and grown in the same medium. The culture at 35° C. rapidly entered exponential growth and the pH was maintained at 5.8 using a caustic potash solution. A 50.5% glucose co-substrate feed was prepared from dextrose monohydrate using the method of Example 5 where the stoichiometric and operating parameters for this feed are given. The co-substrate feed was started near the end of exponential growth phase at a rate of 23.9 kg/hr.

At the end of glucose-limited growth phase, as judged by a rapid decrease in OUR and CER and rapid increase in dissolved oxygen, a 46.6 kg charge of oleic acid was added. This induced the ω-oxidation pathway. The oleic acid feed rate was started about 3 hours later at 18.5 kg/hour and remained constant during the batch to monitor the ω-oxidation kinetics. The temperature was decreased to 30° C. and pH was maintained at 5.8 using a caustic potash solution for the duration of the fermentation. The biomass concentration at induction (biooxidation time 0) was 17.8 g dry weight/kg broth.

Figure 4:
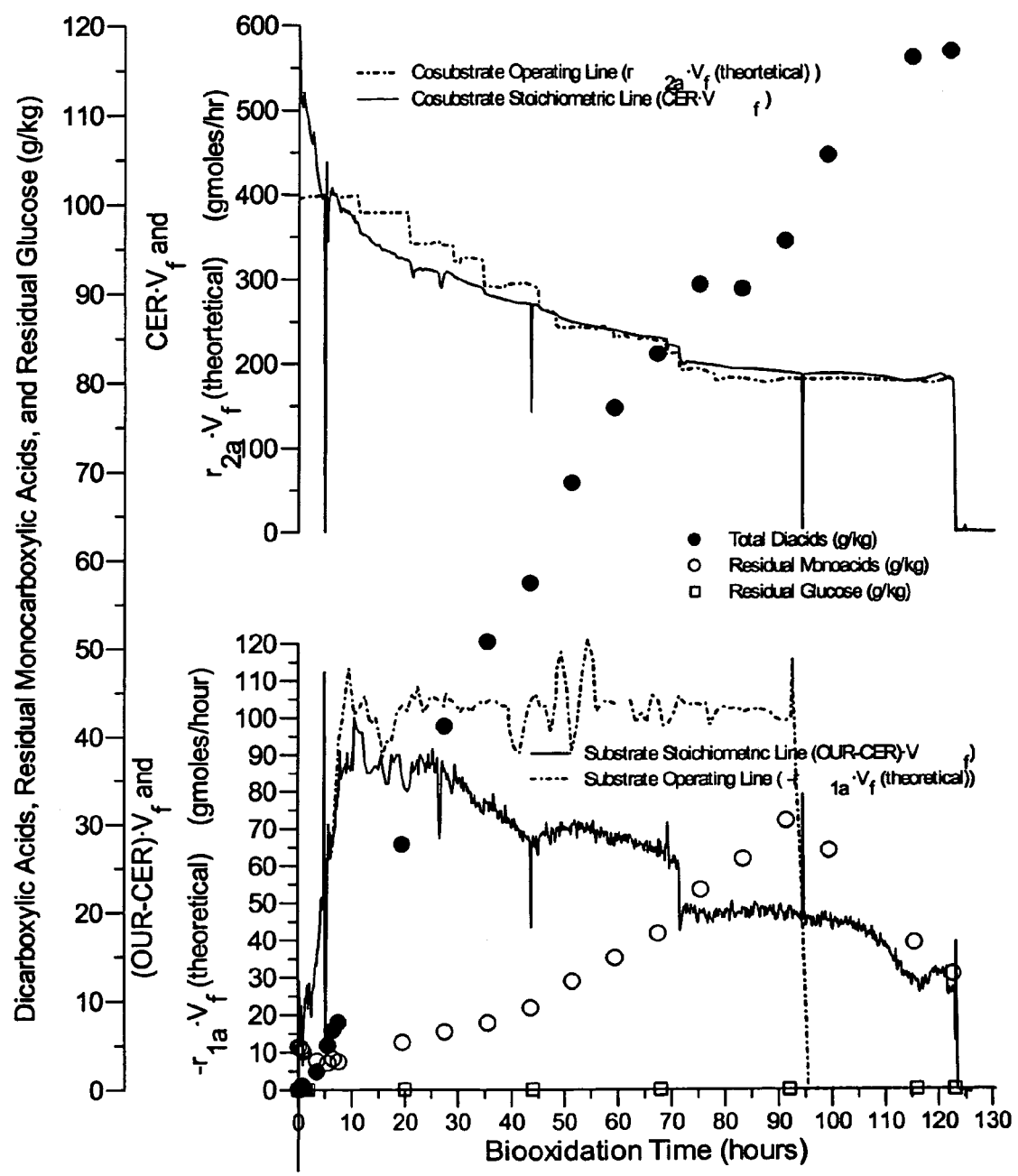
FIG. 4 shows the time course of a biooxidation of commercial oleic acid to dicarboxylic acids, residual glucose levels, and residual fatty acid levels. Also shown is the construction of stoichiometric lines and operating lines for the co-substrate (top) and substrate (bottom).

FIG. 4 shows the time course of this fermentation batch. The glucose feed rate was periodically adjusted in accordance with the formulas of Example 13, effectively using a value of 1 for $A_4$. The ω-oxidation reaction was monitored using the formula of Example 13 and the constant feed rate is represented by the substrate operating line drawn for $b_1/a_1 = 1.5$. The substrate and co-substrate feed rates, $F_s$ and $F_c$ respectively, were monitored by decreases in feed tank levels. Noise spikes in the substrate operating line were due, not to actual fluctuations in feed rate, but rather due to periodic refilling of the small feed tank during the fermentation.

Also shown in FIG. 4 is the accumulation of diacids, unreacted fatty acids, determined by gas chromatography as their methyl ester derivatives. Glucose was not detected in the fermentation samples tested using ion exchange liquid chromatography with a refractive index detector.

The substrate stoichiometric line clearly shows induction of the ω-oxidation pathway over the first 10 hours of the fermentation. That activity decayed over the remainder of that batch. This experiment revealed the significant curvature in the stoichiometric lines, that is the rates of reaction change continuously during the course of the reaction.

In the absence of the techniques of this invention, one is left to only guess at what the feed rates should be; conduct a large number of small scale trials with different feeding schedules that may ultimately have no relevance to a commercial scale reactor; or conduct a large number of offline sample analytical tests then differentiating the analytical results with respect to time to arrive at a prevailing rate (at least what the rate was when the last sample was taken). Then, if a process upset occurs, guess again or wait eight to twelve hours, then grab another sample to see what changes need to be made. We found these methods to be frustratingly time consuming, expensive, and ultimately ineffective in controlling the biooxidation reaction.

There was little biomass accumulation during the batch since the co-substrate feed rate was periodically reduced to only the amount that could be converted to carbon dioxide for energy purposes. Thus no additional carbon was available for growth. The recovery of culturable viable cells was reduced by a factor of ten between induction and the end of the batch, yet the ω-oxidation activity as judged by the substrate stoichiometric line was reduced by only about half. Fatty acids did accumulate during the reaction as would be expected since the operating line was well above the stoichiometric line until the substrate feed ended at about 95 hours into the batch.

EXAMPLE 15

Oxidation of Alkanes and Fatty Acids to Dicarboxylic Acids: Determining Substrate Stoichiometric Parameters from Experimental Data The data from Example 14 are now useful for verifying the stoichiometry of the ω-oxidation pathway by examining the cumulative production of diacids at each sample point and the cumulative consumption of oxygen by the ω-oxidation pathway. That is, for each sample time t, the stoichiometric ratio d1/b1 is given by $$b_1/d_1 = \frac{MW_{diacids} \int_{t=induction}^{t} (r_{1a} \cdot V_f) dt}{X_{diacids} \cdot M(t)} \qquad \text{Equation 15.1}$$

Figure 5:
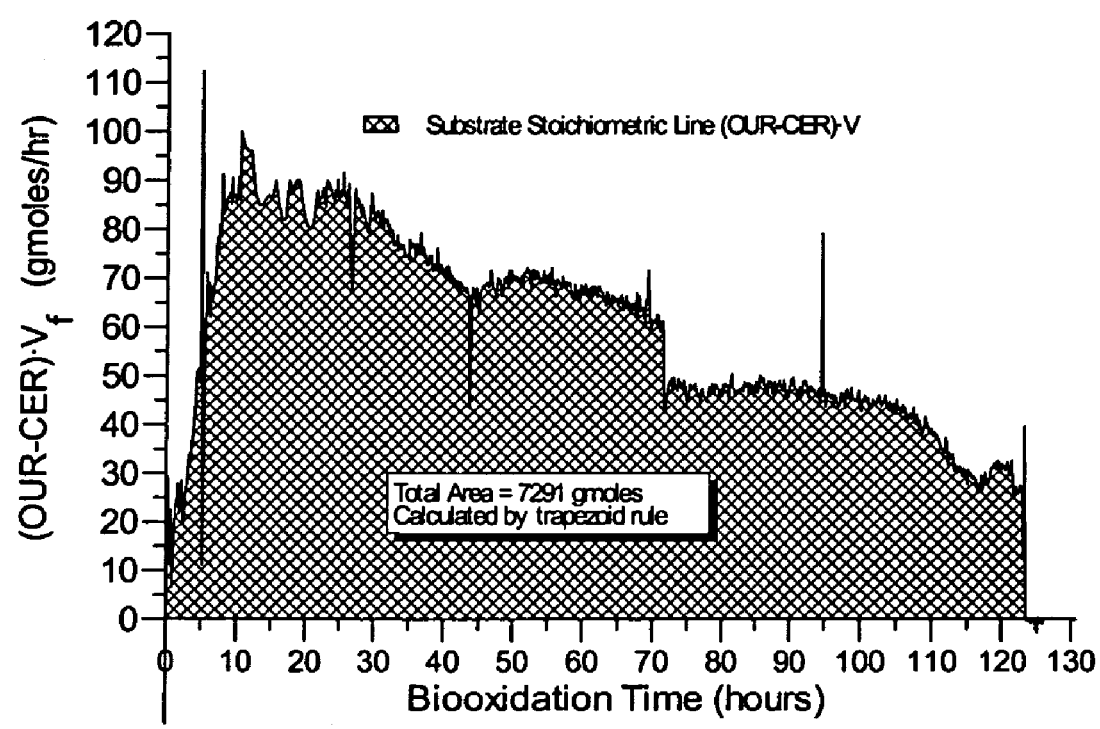
FIG. 5 illustrates numerical integration of the in-line stoichiometric data from FIG. 4 for use in verifying reaction stoichiometry and for estimating product concentrations in the biooxidation reaction mixture.

The integral is evaluated numerically using the in-line substrate stoichiometric line data. This is the area under that curve as shown in FIG. 5 using the data of Example 14, which may be evaluated from the induction time 0 to any later point in time.

Figure 6:
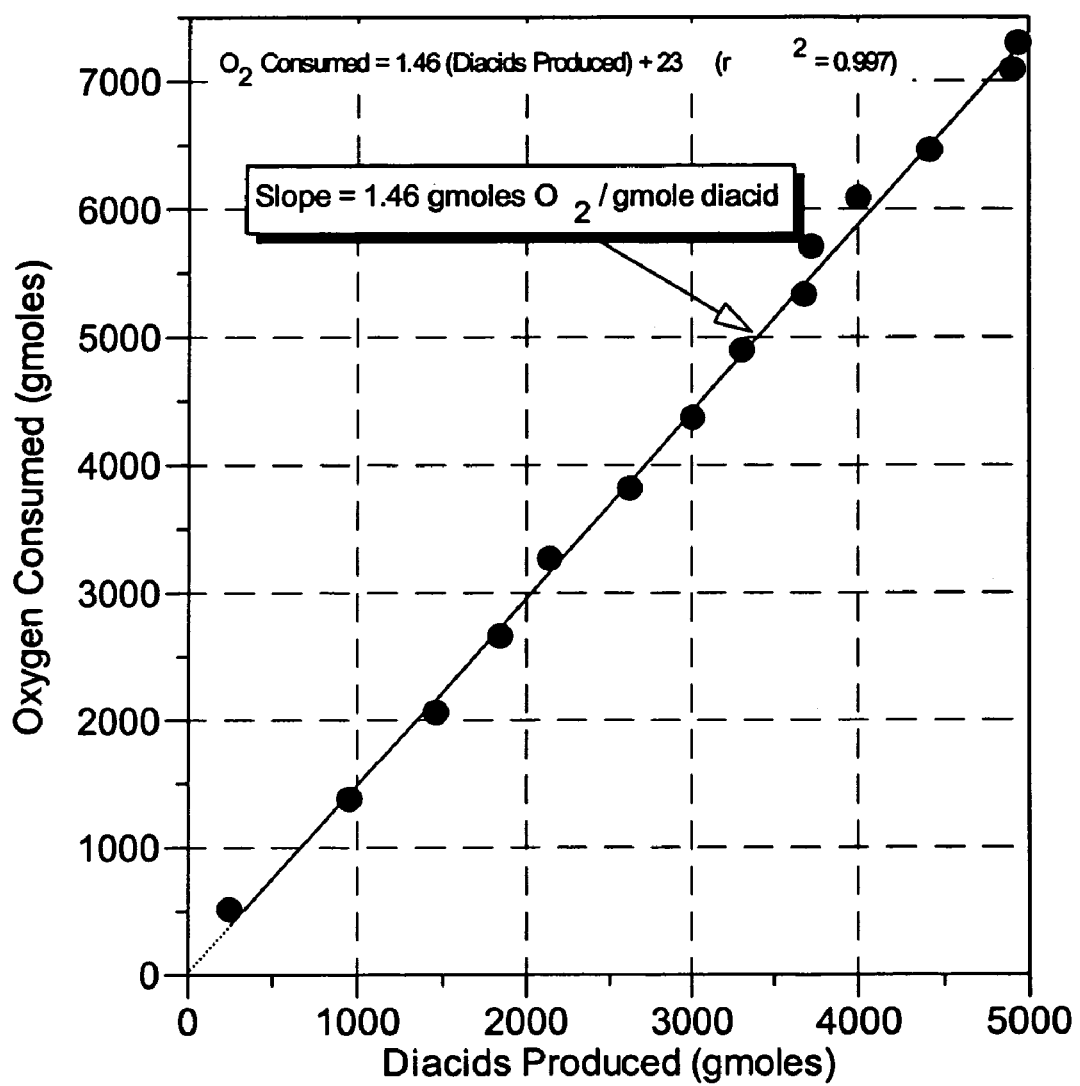
FIG. 6 is a plot of cumulative oxygen consumed by the ω-oxidation pathway versus dicarboxylic acids produced from the data in FIG. 4. The indicated slope verified the overall net stoichiometric coefficient on oxygen in FIG. 3.
Figure 7:
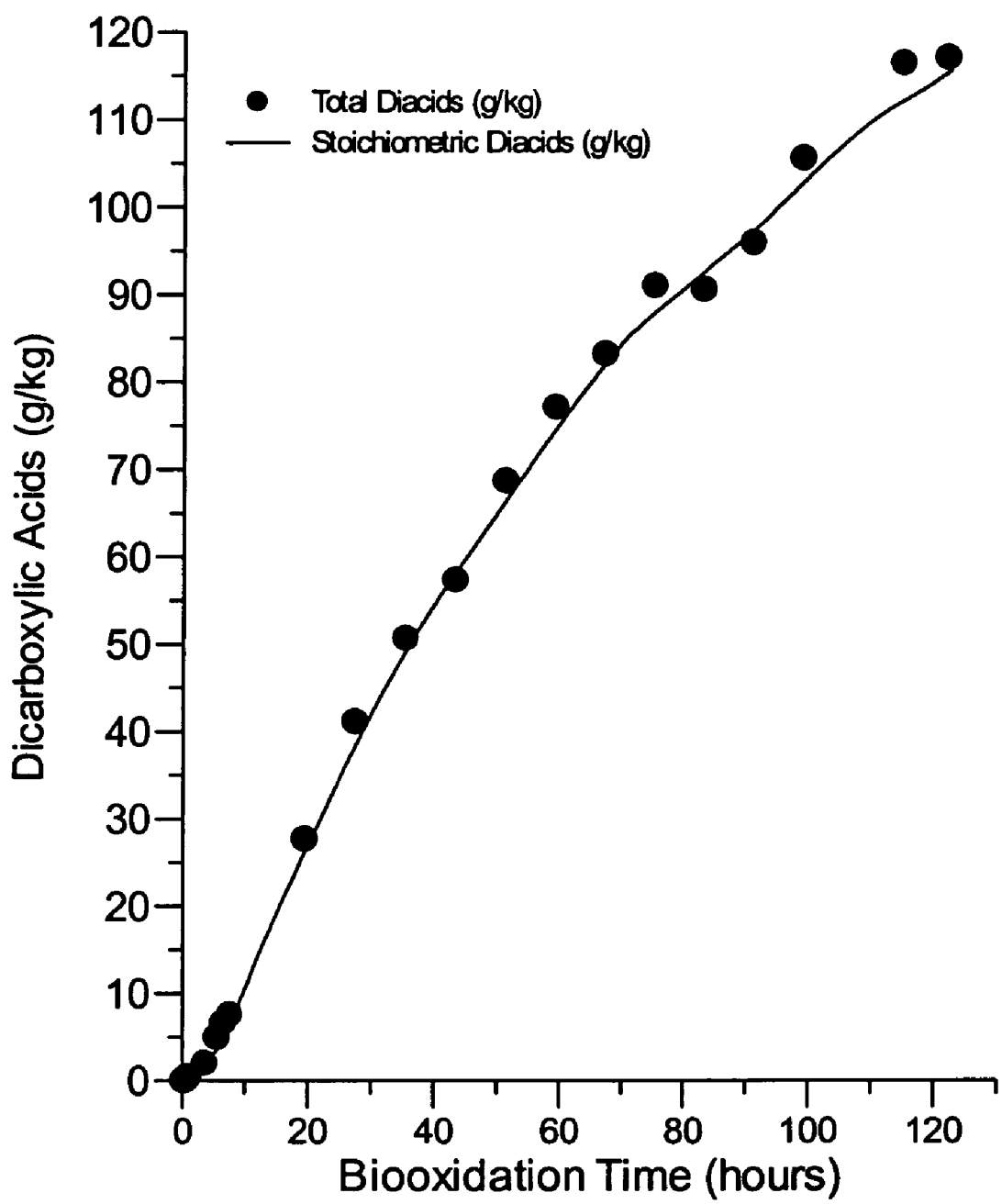
FIG. 7 compares the concentration of dicarboxylic acids in the reaction mixture calculated using the in-line reaction data and stoichiometric calculations with independent offline analysis of samples by gas chromatography.

A plot of cumulative oxygen consumed by ω-oxidation versus diacids produced gives the ratio b1/d1 as shown in FIG. 6 using the data of Example 14. A least-squares fit of that data gives the slope of the line as 1.46 gmoles $O_2$/gmole diacid, very near the expected stoichiometry of 1.5 suggested by the literature data of Example 10.

EXAMPLE 16

Oxidation of Alkanes and Fatty Acids to Dicarboxylic Acids: Determining Substrate Stoichiometric Parameters from Experimental Data Having verified the reaction stoichiometry, it is now possible to make predictions about the composition of the fermentation broth based solely on the in-line data. The diacid concentration is then determined by solving Equation 15.1 for $X_{diacids}$ then conducting the indicated integration of the rate data and collecting vessel working mass data. The result, using the data of Example 14, is shown in FIG. 5 compared with the offline sample analysis. Using this method reduces the need for offline sample analysis.

EXAMPLE 17

Oxidation of an Alkane Substrate to Dicarboxylic acids by ω-Oxidation: Comparative Determination of Reaction Stoichiometry It was useful to further test the ω-oxidation pathway stoichiometry using a substrate having different stoichiometric and operating parameters. An alkane substrate feed was prepared by filter sterilizing NORPAR (a product of Exxon) alkanes into a sterile feed container. Table 17.1 shows the composition of this alkane substrate obtained by gas chromatography. The average molecular weight of the alkanes in this mixture was 186.6. In contrast to the fatty acid substrate of Example 12, where only one pass through the ω-oxidation pathway to make the corresponding diacids, the alkane requires two passes. Then three moles of oxygen are needed to oxidize one mole of substrate to one mole of product. The stoichiometric parameters for substrate oxidation Reaction 1, using the ω-oxidation stoichiometry of Example 10 and FIG. 3, for $a_1=1$, $b_1=3$, $c_1=0$ $d_1=1$, $e_1=0$, $f_1=1$.

A biooxidation was conducted using this alkane substrate with a glucose feed similar to that used for Example 14 though at about one-tenth the fermentation scale. The control formulas of Example 13, subject to the stoichiometric and operating parameters for this substrate determined above, were used to monitor the bioxidation and control the glucose feed.

Figure 8:
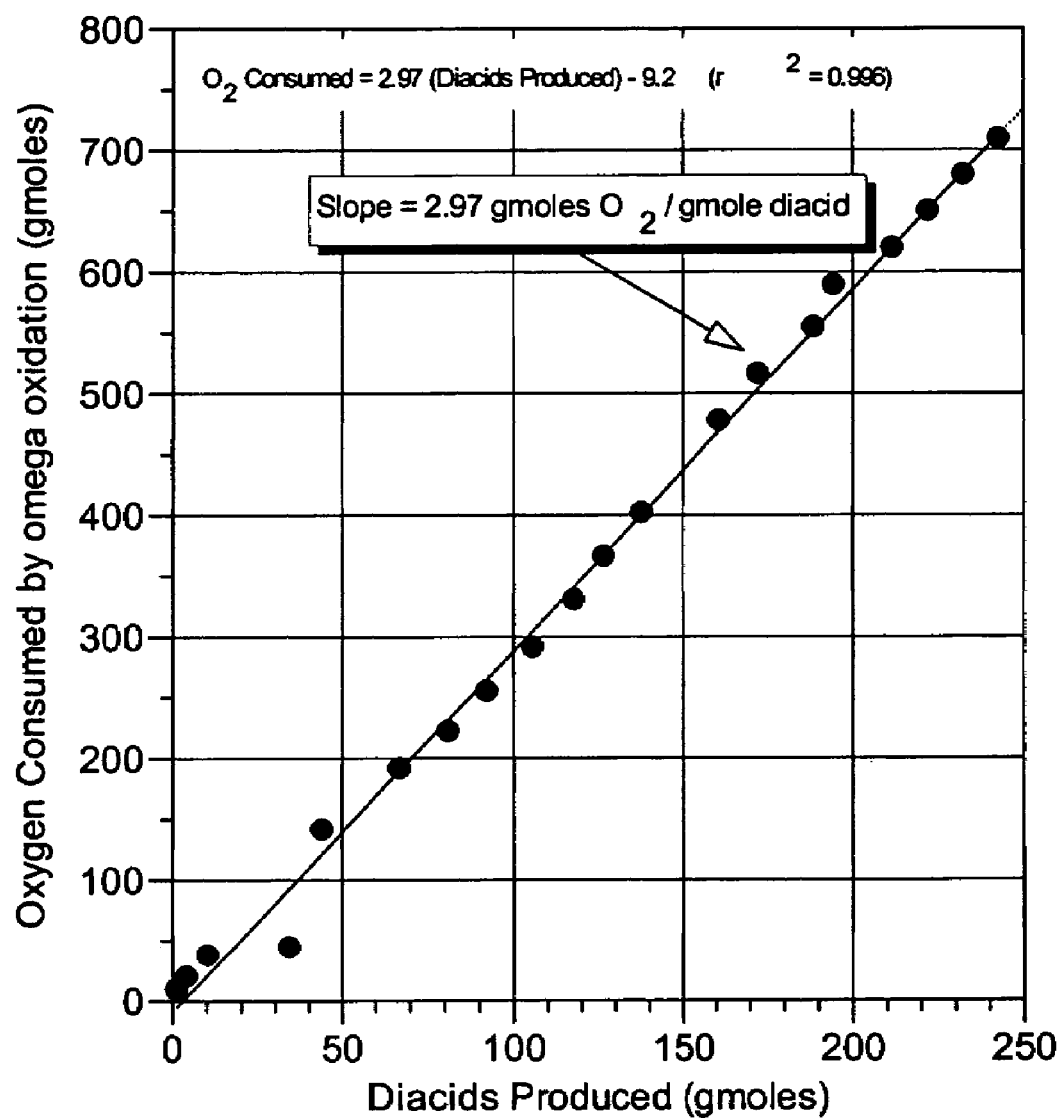
FIG. 8 is a plot of cumulative oxygen consumed by the ω-oxidation pathway versus dicarboxylic acids produced for the conversion of alkanes to dicarboxylic acids. Alkanes require two passes through the ω-oxidation pathway requiring three moles of oxygen.

FIG. 8 shows the data plotted according to the method of Example 15 to give the ratio $b_1/d_1=2.97$ gmoles $O_2$/gmole diacid. This is consistent with two passes through the ω-oxidation pathway of FIG. 3.

TABLE 17.1

Composition of NORPAR Hydrocarbon Substrate.

| Component Fatty Acid | Weight % |
| --- | --- |
| undecane | 0.2 |
| dodecane | 14.1 |
| tridecane | 52.5 |
| tetradecane | 32.4 |
| pentadecane | 0.6 |

EXAMPLE 18

Oxidation of an Oleic Acid Substrate to Dicarboxylic Acids by ω-Oxidation using a Glucose Co-Substrate: Simultaneously Controlling the Substrate and Co-Substrate Feed A fermentor was charged with 86 metric tons of synthetic growth medium as described in copending application Ser. No. 09/663,963. The medium was inoculated with 1.4 metric tons of an actively growing culture of a β-oxidation blocked *Candida tropicalis* yeast grown in a complex glucose/yeast extractpeptone medium. The culture at 35° C. rapidly entered exponential growth and the pH was maintained at 5.8 gaseous ammonia. A 45.2% glucose co-substrate feed was prepared using the method of Example 6 where the stoichiometric and operating parameters for this feed are given. The co-substrate feed was started near the end of exponential growth phase at a rate of 250 kg/hr.

An oleic acid substrate feed similar to the method of Example 12 was prepared except this feed was sterilized by direct steam heating. As a result, this feed contained about 17.7% steam condensate. Therefore the operating parameter, $X_S$, for this feed was 0.82. The other operating and stoichiometric parameters were the same.

At the end of glucose-limited growth phase, as judged by a rapid decrease in OUR and CER and rapid increase in dissolved oxygen, a 410 kg charge of the oleic acid substrate feed was added. This induced the ω-oxidation pathway. The oleic acid substrate feed rate was started by periodically adding charges of the substrate feed to give a time-average feed rate of about 140 kg/hr. The period used for these substrate feed additions was typically 1-3 hours. The temperature was decreased to 30° C. and pH was maintained at 5.8 using a caustic soda solution for the duration of the fermentation. The biomass concentration at induction (biooxidation time 0) was 19.2 g dry weight/kg broth.

Figure 9:
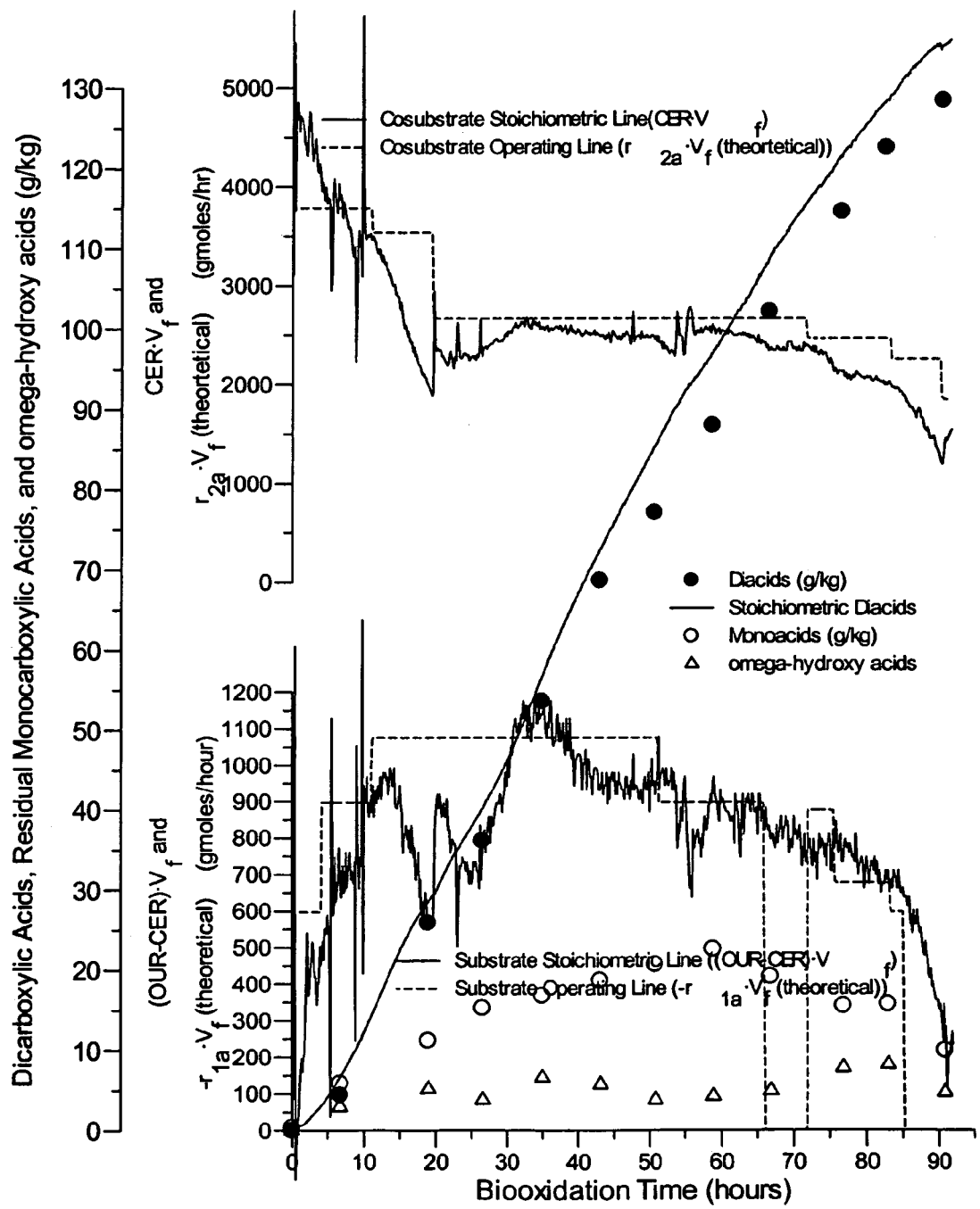
FIG. 9 shows the time course of a biooxidation of commercial oleic acid to dicarboxylic acids.

FIG. 9 shows the time course, including the yield, for this biooxidation reaction. The co-substrate feed rate was periodically adjusted as needed in response to the stoichiometric line trends. Similarly the oleic acid feed rate was increased in response to the substrate stoichiometric line data, here in three steps over the first ten hours.

This batch did enter a phase between hour 10 and about hour 25 where unfavorable rheological characteristics developed and the ω-oxidation activity declined. The substrate feed rate was not changed however, because it was found that allowing the residual oleic acid to accumulate helped mitigate the unfavorable broth rheology. This phenomena is barely perceptible from the trend in the offline data (a differential method), which might be attributed to random scatter in the data. The overall effect on ω-oxidation activity, however is quite pronounced as judged by the sensitive integral methods of this invention.

As the batch progressed, the substrate feed rate was decreased in response to the substrate stoichiometric line to stop further accumulation of unreacted substrate. Loss of substrate feed between hour 66 and hour 72 was an unplanned process upset that, in this case had little effect on the biooxidation reaction. The final biomass concentration observed at the end of the batch was 8.4 g/kg. Overall, this biooxidation consumed 0.54 kilograms of glucose (anhydrous basis) feed for each kilogram of diacid produced.

The broth diacid concentration calculated using the method of Example 16 agreed closely with the concentrations independently determined by gas chromatography. It was later found that the agreement improved significantly if the oxygen consumed to make the small amount of accumulated ω-hydroxyacids was considered in constructing the stoichiometric diacids curve.

In this example, the values of A3 and A4 varied during the batch since the necessary adjustments co-substrate and substrate feed rates, respectively, were made at infrequent intervals. The substrate served multiple purposes in this biooxidation in that it not only was the substrate for the biooxidation, but was also the inducer of the biooxidation pathway and served some broth viscosity modification functions. Therefore, it was useful to allow the accumulation of some residual fatty acid substrate during the early part of the batch by operating with A4 greater than 1. Later in the batch, to reduce the accumulated monoacids, A4 was effectively decreased to 1, then to zero to convert the residual monoacids. More frequent adjustment intervals are possible if desirable to limit substrate accumulation. We have found that feed rate control at the level of the noise in the component gas balance data to not be desirable. It is useful in these cases to either apply a smoothing technique to the data or choose an appropriate deadband for making the adjustments.

COMPARATIVE EXAMPLE 1

Oxidation of an Oleic Acid Substrate to Dicarboxylic acids by ω-Oxidation using a Glucose Co-Substrate: No Substrate or Co-Substrate Feed Rate Control The methods of this invention have provided much useful insight into the operating characterizes of the biooxidation reaction. Prior to this however, the reaction was simply run with by using a constant co-substrate feed rate or by empirically developing a set of scheduled co-substrate feed rate changes. Offline analysis of residual glucose proved impractical because the concentration was immeasurably low. Adjustments to the substrate feed rate were frequently made, either in response to an offline gas chromatography analysis of the broth or likewise on an empirically determined schedule.

A β-oxidation blocked diacid producing strain of *Candida tropicalis* was grown on glucose to a density of about 18 g/kg in a basis volume of 10 kg of fermentation broth. A co-substrate feed of 50% glucose in water was made from dextrose monohydrate and fed to the culture near the end of growth phase at 36 grams/hour. This co-substrate feed rate was maintained constant through the remainder of the batch.

Figure 10:
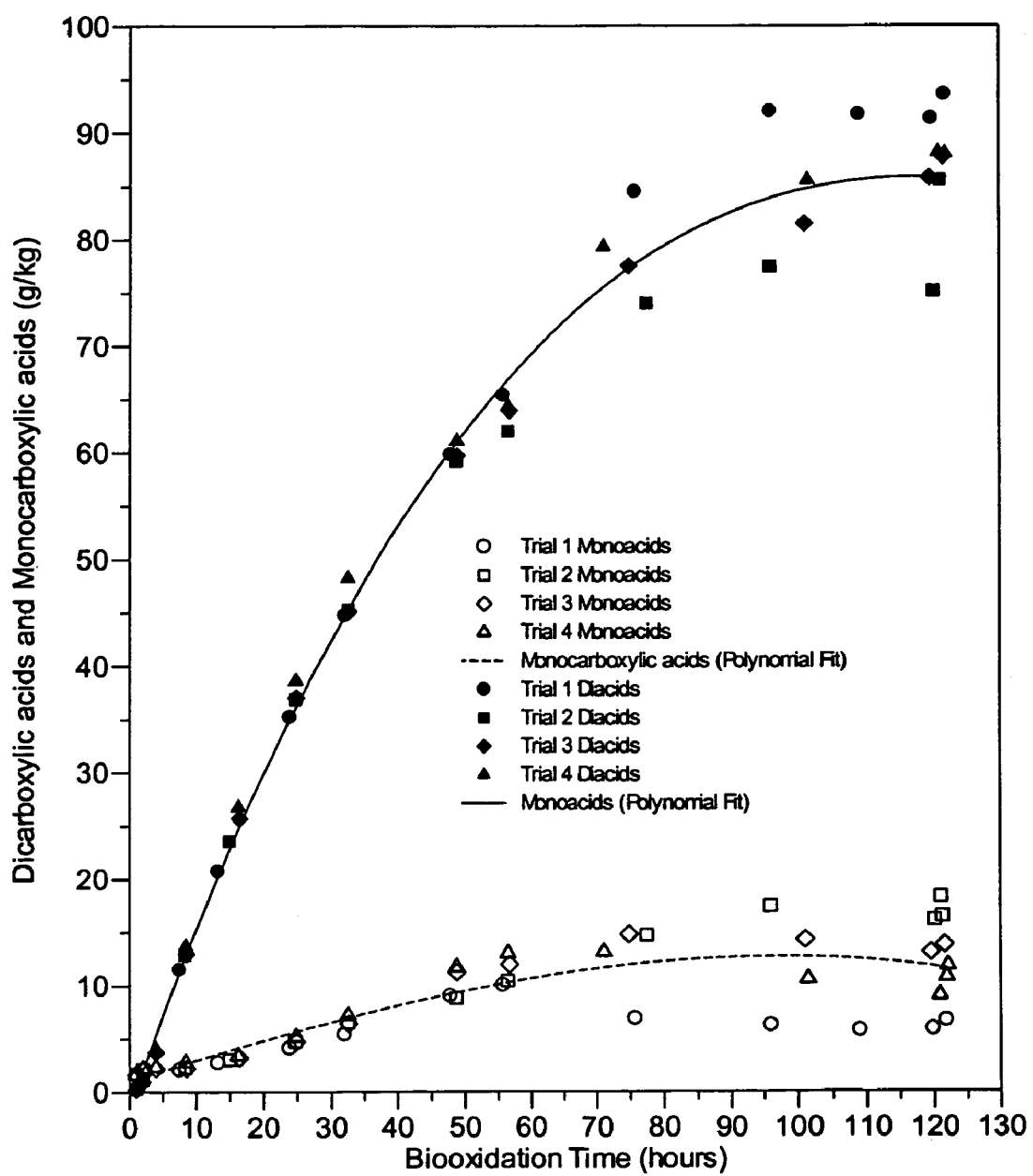
FIG. 10 shows the time course of a biooxidation of commercial oleic acid to dicarboxylic acids without control of the biooxidation reaction.

An EMERSOL® oleic acid substrate feed was started when the glucose used to grow the cells was depleted as judged by a rapid increase in dissolved oxygen. This induced the ω-oxidation pathway. The oleic acid substrate feed rate was initially set at 18 g/hr, but was reduced to 15 g/hr about 48 hours into the biooxidation reaction. The substrate feed was stopped completely about 90 hours into the batch. FIG. 10 shows the accumulation of diacids and monoacids during four separate trials.

The production of diacids was initially good but slowed as the batch progress. Overall the biooxidation reaction operated in this uncontrolled manner consumed 1.7 kg of glucose for each kg of diacid produced. Closer examination showed that biomass had accumulated to about 45.5 g dry weight/kg broth. Infrared spectroscopy of the dried biomass sample showed it was comprised of 13% to 16% triacylglycerol fatty acid esters. Thus side reactions involving both the substrate and co-substrate occurred with this uncontrolled operation.

COMPARATIVE EXAMPLE 2

Oxidation of an Oleic Acid Substrate to Dicarboxylic Acids by ω-Oxidation using a Glucose Co-Substrate: Excessive Addition of Substrate A biooxidation reaction was set up similar to the method of Example 18 wherein the co-substrate was controlled by periodic adjustment of the cosubstrate feed rate to the co-substrate stoichiometric line. An excessive amount of substrate (up to 90 g/kg residual monoacids) was added during the first 10 hours of the biooxidation reaction. After 21 hours of biooxidation time, the broth contained only 14 g/kg dicarboxylic acids, but the ω-hydroxyacid intermediate produced from the first step of the ω-oxidation pathway (refer to FIG. 3) had accumulated to 13 g/kg. Thus the lack of substrate feed rate control reduced productivity and led to the diversion of substrate to the accumulation of a biooxidation reaction intermediate.

What is claimed is:

1. A method for controlling a biooxidation reaction for preparing carboxylic acids comprising the steps of:
   (1) independently adding a substrate and a co-substrate at predetermined rates to a biooxidation reaction mixture comprised of a biocatalyst;
   (2) measuring the oxygen consumption rate and carbon dioxide evolution rate from the reaction mixture;
   (3) determining the instantaneous rates of substrate $(-r_s)$ and co-substrate consumption $(-r_c)$ by solving simultaneous equations relating carbon dioxide evolution rate and oxygen consumption rate to the substrate oxidation stoichiometry, of the form,

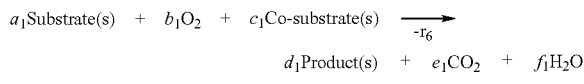

the co-substrate combustion stoichiometry of the form,

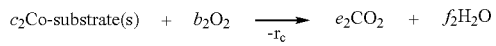

and a constitutive stoichiometric model for the yield of biomass formation having anabolic reactions of the form,

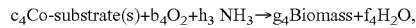

wherein, the simultaneous equations are given by $$-r_6 = \frac{-r_{O2} - (b_2/e_2)r_{CO2}}{(b_1/a_1) - (b_2/e_2)(e_1/a_1) + (b_4/g_4)(d_1/a_1)\Psi}$$

$-r_c = [(c_4/g_4)(d_1/a_1)\Psi + (c_1/a_1) - (c_2/e_2)(e_1/a_1)](-r_s) + (c_2/e_2)r_{CO2}$, and $\Psi = (MW_P/MW_X)(1/Y_{P/X})[1 - Y_{P/X}]$ (4) simultaneously adjusting the substrate and co-substrate addition rates, either continuously or periodically during the biooxidation reaction, relative to the rates of substrate oxidation and co-substrate consumption according to the control formulas $F_s(\text{setpoint}) = A_1(Mw_s/X_s)(-r_s)V_f$ and $F_c(\text{setpoint}) = A_2(Mw_c/X_c)(-r_c)V_f$ respectively, using dimensionally consistent units of measure, thereby maximizing the rate of product formation while minimizing the rate of co-substrate usage, using adjustable parameters $A_1$ and $A_2$ having values of about 1 depending upon the phase of biooxidation, wherein the variables are defined by

| Symbol | Definition |
| --- | --- |
| $A_1$ | Ratio substrate feed to substrate demand, slope of substrate operating line |
| $A_2$ | Ratio co-substrate feed to co-substrate demand, slope of co-substrate operating line |
| $F_s(\text{setpoint})$ | Substrate feed rate setpoint |
| $F_C(\text{setpoint})$ | Co-substrate feed rate setpoint |
| $r_{CO2}$ | Rate of carbon dioxide evolution; CER |
| $-r_{O2}$ | Rate of oxygen consumption; OUR |
| $-r_C$ | rate of co-substrate consumption |
| $-r_S$ | rate of substrate consumption |
| $Y_{P/X}$ | mass of product in a unit mass of dry biomass |
| $Mw_c$ | formula weight of the co-substrate |
| $Mw_X$ | formula weight of biomass |
| $Mw_S$ | formula weight of substrate |
| $MW_{diacids}$ | formula weight of diacids (Example 15) |
| $X_c$ | Mass fraction metabolizable substances in the co-substrate feed |
| $X_s$ | Mass fraction metabolizable substances in the substrate feed |
| $V_f$ | biooxidation reaction mass |
| $a_i$ | Stoichiometric coefficient of substrate in reaction i |
| $b_i$ | Stoichiometric coefficient of oxygen in reaction i |
| $c_i$ | Stoichiometric coefficient of co-substrate in reaction i |
| $d_i$ | Stoichiometric coefficient of products in reaction i |
| $e_i$ | Stoichiometric coefficient of carbon dioxide in reaction i |
| $f_i$ | Stoichiometric coefficient of water in reaction i |
| $g_i$ | Stoichiometric coefficient of biomass in reaction i |
| $h_i$ | Stoichiometric coefficient of ammonia in reaction i |
| $\Psi$ | Molar ratio of product to biomass |

2. The method of claim 1 wherein the substrate is a carboxylic acid.

3. The method of claim 2 wherein the carboxylic acid is oleic acid.

4. The method of claim 1 wherein the substrate is an alkane.

5. The method of claim 1 wherein the co-substrate is glucose.

6. The method of claim 1 for controlling a biooxidation reaction for making an $\alpha,\omega$-dicarboxylic acid comprising the steps of:

(1) independently adding a substrate selected from the group consisting of an alkane, an alkene, an alcohol, an aldehyde, a carboxylic acid or a derivative thereof and a co-substrate at independently predetermined rates to a biooxidation reaction mixture comprised of a biocatalyst for converting the substrate to the $\alpha,\omega$-dicarboxylic acid;

(2) measuring the oxygen consumption rate and carbon dioxide evolution rate of the reaction mixture;

(3) determining the instantaneous rates of substrate and co-substrate consumption by solving the simultaneous equations relating carbon dioxide evolution rate and oxygen consumption rate to the substrate oxidation stoichiometry, the co-substrate combustion stoichiometry, and optionally the biomass formation stoichiometry;

(4) simultaneously adjusting the substrate and co-substrate addition rates to the rates of substrate oxidation and co-substrate consumption, whereby the rate of formation of the $\alpha,\omega$-dicarboxylic acid is maximized while simultaneously minimizing the rate of co-substrate usage.

7. The method of claim 6 wherein the substrate is an alkane.

8. The method of claim 6 wherein the substrate is a carboxylic acid.

9. The method of claim 8 wherein the carboxylic acid is oleic acid.

10. The method of claim 4 wherein the co-substrate is glucose.

11. The method of claim 1 wherein the biocatalyst is *Candida tropicalis* H 5343.

12. The method of claim 6 wherein the biocatalyst is *Candida tropicalis* H 5343.

13. A method for making an 9-octadecenedioic acid comprising the steps of:

(1) independently adding a commercial oleic acid and a commercial glucose solution at predetermined rates to a biooxidation reaction mixture comprised of *Candida tropicalis* H 5343;

(2) measuring the oxygen consumption rate ($-r_{O2}$=OUR) and carbon dioxide evolution rate ($r_{CO2}$=CER) from the reaction mixture;

(3) determining the instantaneous rates of oleic acid consumption and glucose consumption by solving simultaneous equations relating carbon dioxide evolution rate and oxygen consumption rate to the oleic acid oxidation stoichiometry, the of the form,

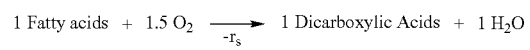

and glucose combustion stoichiometry of the form,

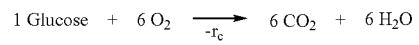

according to $-r_s \cdot v_f = (1/1.5)(-r_{O2} - r_{CO2}) \cdot V_f$ and $-r_c \cdot V_f = (1/6)(-r_{CO2} \cdot V_f)$ respectively;

(4) adjusting continuously or periodically during the biooxidation reaction the oleic acid and glucose addition rates relative to the rates of oleic acid oxidation and glucose consumption according to $$F_s(\text{set point}) = A_3(Mw_s/X_s) - r_s \cdot V_f$$

and $$F_c(\text{set point}) = A_4(Mw_c/X_c) - r_c \cdot V_f$$

wherein the values of $A_3$ and $A_4$ are about 1 in order to maximize the rate of the 9-octadecenedioic acid formation while simultaneously minimizing the rate of glucose usage where the variables are defined by

| Symbol | Definition |
|---|---|
| $A_3$ | Ratio of commercial oleic acid feed to oleic acid demand |
| $A_4$ | Ration of glucose feed solution to glucose solution demand |
| $F_s$(setpoint) | Substrate feed rate setpoint |
| $F_C$(setpoint) | Co-substrate feed rate setpoint |
| $r_{CO2}$ | Rate of carbon dioxide evolution; CER |

-continued

| Symbol | Definition |
|---|---|
| $-r_{O2}$ | Rate of oxygen consumption; OUR |
| $-r_C$ | rate of co-substrate consumption |
| $-r_S$ | rate of substrate consumption |
| $Mw_c$ | formula weight of the co-substrate |
| $Mw_S$ | formula weight of substrate |
| $X_c$ | Mass fraction metabolizable substances in the co-substrate feed |
| $X_s$ | Mass fraction metabolizable substances in the co-substrate feed |
| $V_f$ | biooxidation reaction mass |

, whereby, the formation of 9-octadecenedloic acid is maximized and the glucose usage is minimized.

14. The method of claim 1 wherein the rate of biomass production is 0 and the value of $\Psi$ is set to 0.

* * * * *